(12) United States Patent
Lindsey et al.

(10) Patent No.: US 7,423,160 B2
(45) Date of Patent: Sep. 9, 2008

(54) BORON COMPLEXATION STRATEGY FOR USE IN MANIPULATING 1-ACYLDIPYRROMETHANES

(75) Inventors: Jonathan S. Lindsey, Raleigh, NC (US); Kannan Muthukumaran, Raleigh, NC (US); Marcin Ptaszek, Raleigh, NC (US); H. Z. Syeda Huma, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 11/846,630

(22) Filed: Aug. 29, 2007

(65) Prior Publication Data

US 2008/0027232 A1 Jan. 31, 2008

Related U.S. Application Data

(62) Division of application No. 11/559,138, filed on Nov. 13, 2006, now Pat. No. 7,282,582, which is a division of application No. 10/872,321, filed on Jun. 18, 2004, now Pat. No. 7,153,975.

(51) Int. Cl.
*C07D 207/00* (2006.01)
(52) U.S. Cl. ..................................... 548/405
(58) Field of Classification Search ........................ None
See application file for complete search history.

(56) References Cited

U.S. PATENT DOCUMENTS

| 6,420,648 | B1 | 7/2002 | Lindsey |
| 6,559,374 | B2 | 5/2003 | Lindsey et al. |
| 6,603,070 | B2 | 8/2003 | Lindsey et al. |
| 6,642,376 | B2 | 11/2003 | Lindsey et al. |
| 6,924,375 | B2 | 8/2005 | Lindsey et al. |
| 2003/0096978 | A1 | 5/2003 | Lindsey et al. |
| 2005/0282779 | A1 | 12/2005 | Lindsey et al. |

OTHER PUBLICATIONS

Zaidi et al., "9-Acylation of 1-Acyldipyrromethanes Containing a Dialkylboron Mask for the Acylpyyrole Motif," J. Organic Chem., vol. 69, No. 24, pp. 8356-8365 (2004).
Muthukumaran et al., "Boron-Complexation Strategy for Use with 1-Acyldipyrromethanes", *The Journal of Organic Chemistry*, 2004, vol. 69 (16), p. 5354-5364.
Zaidi et al., "9-Acylation of 1-Acyldipyrromethanes Containing a Dialkylboron Mask for the α-Acylpyrrole Motif", *The Journal of Organic Chemistry*, 2004, vol. 69 (24), p. 8356-8365.
U.S. Appl. No. 10/641,412, filed Aug. 15, 2003, Lindsey et al.
Gryko et al.; "Parallel synthesis of *meso*-substituted corroles and *meso*-substituted [22]pentaphyrins(1.1.1.0.0) from diacyldipyrromethanes" *J. Porphyrins Phthalocyanines* 7 239-248 (2003).
Rao et al.; "Rational Syntheses of Porphyrins Bearing up to Four Different Meso Substituents" *J. Org. Chem.* 2000 65, 7323-7344 (2000).

*Primary Examiner*—Kamal Saeed
*Assistant Examiner*—Sun Jae Y Loewe
(74) *Attorney, Agent, or Firm*—Myers Bigel Sibley & Sajovec, P.A.

(57) ABSTRACT

A method of making a metal complex comprises combining a 1-monoacyldipyrromethane with a compound of the formula $R^1R^2MX$, wherein M is boron, $R^1$ and $R^2$ are each independently organic substituents; and X is an anion leaving group; to produce a metal complex of the formula $DMR^1R^2$ wherein DH is a 1-monoacyldipyrromethane. The methods and complexes are useful for the purification and synthesis of dipyrromethanes and porphyrins.

7 Claims, 1 Drawing Sheet

BORON COMPLEXATION STRATEGY FOR USE IN MANIPULATING 1-ACYLDIPYRROMETHANES

RELATED APPLICATIONS

This application is a divisional of U.S. patent application Ser. No. 11/559,138, filed Nov. 13, 2006 now U.S. Pat. No. 7,282,582; which is a divisional of U.S. patent application Ser. No. 10/872,321, filed Jun. 18, 2004, now U.S. Pat. No. 7,153,975; the disclosures of which are incorporated by reference herein in their entirety.

This application is also related to U.S. patent application Ser. No. 10/956,781, filed Oct. 1, 2004, which is a continuation in part of parent application Ser. No. 10/872,321 (now U.S. Pat. No. 7,153,975).

This application is also related to U.S. patent application Ser. No. 10/654,181, filed Sep. 3, 2003, now U.S. Pat. No. 6,924,375, titled Facile Synthesis of 1,9-Diacyldipyrromethanes; and 10/698,255, filed Oct. 31, 2003, now U.S. Pat. No. 7,148,361, titled Synthesis of Phosphono-substituted Porphyrin Compounds for Attachment to Metal Oxide Surfaces, the disclosures of which are incorporated by reference herein in their entirety.

This invention was made with Government support under grant number GM36238 from the National Institutes of Health. The United States government has certain rights to this invention.

FIELD OF THE INVENTION

This invention concerns methods and intermediates useful for the synthesis of 1-acyldipyrromethanes, along with methods of use thereof.

BACKGROUND OF THE INVENTION

Rational syntheses of a variety of porphyrinic compounds bearing diverse patterns of meso substituents have been developed recently. The porphyrinic compounds include porphyrins,[1-3] chlorins,[4] corroles,[5] and bilanes.[6] The syntheses begin with dipyrromethanes (1), and, depending on desired substitution pattern, also employ 1-acyldipyrromethanes (2) and 1,9-diacyldipyrromethanes (3) (Chart 1).[1,2] 1-Acyldipyrromethanes are readily prepared from the corresponding dipyrromethane, while 1,9-diacyldipyrromethanes can be prepared by 9-acylation of a 1-acyldipyrromethane or by 1,9-diacylation of a dipyrromethane. Although the acylation procedures work reasonably well, purification is difficult owing to the lack of crystallinity of the acyldipyrromethanes. Accordingly, the mixture containing the acyldipyrromethane is usually separated by chromatography, which can be tedious owing to the tendency of the acyldipyrromethanes to streak on chromatographic media.

Chart 1

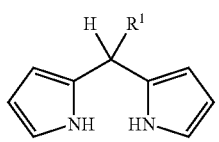

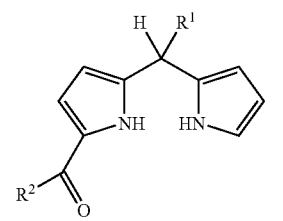

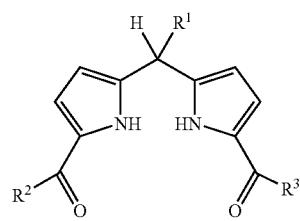

One of our objectives over the past few years has been to increase the scale of porphyrin syntheses, which entails decreasing if not eliminating reliance on chromatography for purification. Toward this goal, we recently developed a simple procedure for isolating a 1,9-diacyldipyrromethane from the diacylation reaction mixture by forming a dialkyltin complex (Chart 2).[7] Dipyrromethanes, 1-acyldipyrromethanes or 1,8-diacyldipyrromethanes did not give tin complexes. The tin complex of a 1,9-diacyldipyrromethane was hydrophobic and crystalline, greatly facilitating isolation. In addition, the tin complex readily underwent decomplexation upon treatment with dilute trifluoroacetic acid. The availability of the tin-complexation procedure has enabled routine synthesis of multigram quantities of 1,9-diacyldipyrromethanes.

Chart 2

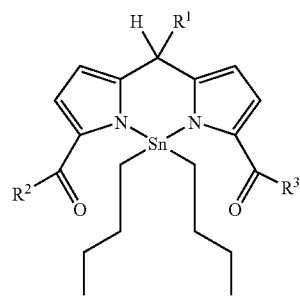

SUMMARY OF THE INVENTION

We herein describe the development of a boron-complexation strategy for the isolation and purification of 1-acyldipyrromethanes formed upon acylation of dipyrromethanes. We also describe use of the 1-acyldipyrromethane-boron complexes in porphyrin-forming reactions following similar procedures employed with 1-acyldipyrromethanes. The ability to complex the 1-acyldipyrromethane greatly facilitates purification and enables synthesis of 1-acyldipyrromethanes at the multigram scale.

Thus, a first aspect of the present invention is a method of making a metal complex, comprising: (a) providing a 1-monoacyldipyrromethane; and then (b) combining (e.g., in a suitable solvent such as dichloromethane) said 1-monoacyldipyrromethane with a compound of the formula $R^1R^2MX$, wherein M is boron, $R^1$ and $R^2$ are each independently organic substituents (preferably substituents in which M is coupled by covalent link to a carbon atom in the organic substituents); and X is an anion leaving group; to produce a metal complex of the formula $DMR^1R^2$ wherein DH is said 1-monoacyldipyrromethane.

A further aspect of the present invention is a 1-monoacyldipyrromethane-boron complex of the formula $DMR^1R^2$, wherein: DH is a 1-monoacyldipyrromethane, M is boron, and $R^1$ and $R^2$ are as described above, and in further detail below. The complex may be provided in solid form, including crystal solid form.

A further aspect of the present invention is a method of making a porphyrin, comprising: providing a 1-monoacyldipyrromethane-boron complex as described herein, and then reducing said 1-monoacyldipyrromethane in said complex without prior decomplexation of said boron to produce said porphyrin.

A further aspect of the present invention is a method of making a 1,9-diacyldipyrromethane metal complex, comprising: providing a 1-monoacyldipyrromethane-boron complex as described herein; and then acylating said 1-monoacyldipyrromethane in said complex at the 9 position with a pyridyl thioate Mukaiyama reagent in the presence of a Grignard reagent and a base to produce said 1,9-diacyldipyrromethane metal complex.

A further aspect of the present invention is a method of making a compound useful as a chlorin eastern half, comprising: providing a 1-monoacyldipyrromethane-boron complex as described above, and then halogenating (e.g., brominating) said 1-monoacyldipyrromethane in said complex at the 9 position to produce a 1-acyl-9-halodipyrromethane-boron complex useful as a chlorin eastern half.

DETAILED DESCRIPTION OF THE PREFERRED EMBODIMENTS

Figure 1:
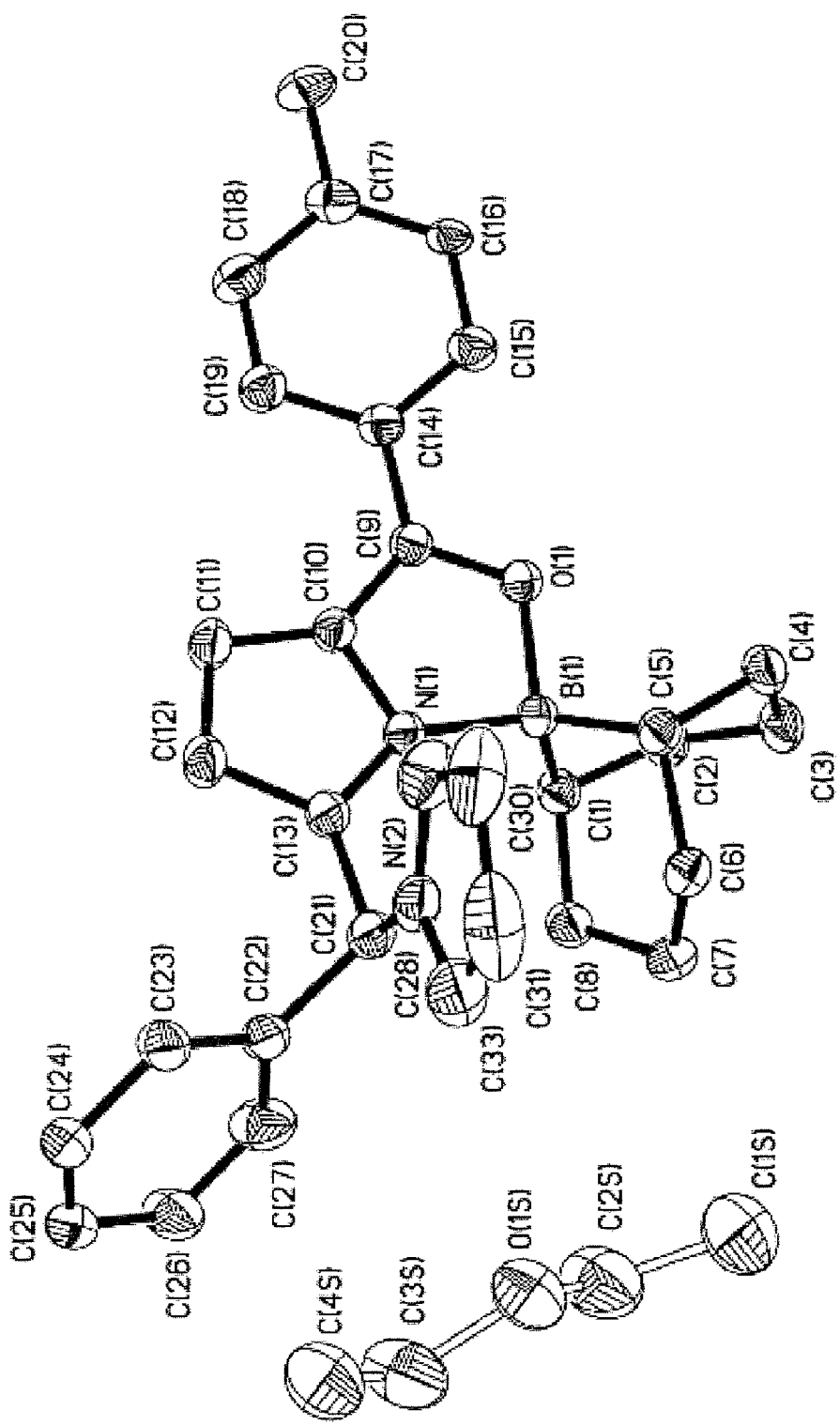
FIG. 1 shows an ORTEP drawing of the X-ray structure of a 1-acyldipyrromethane-boron complex of the present invention (compound 6a-BBN). The diethyl ether solvate molecule is also illustrated. All ellipsoids are contoured at the 50% level, and hydrogens are omitted for clarity.

The present invention is explained in greater detail below. This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

"Alkyl," as used herein, refers to a straight or branched chain hydrocarbon containing from 1 to 10 or 20 carbon atoms, or more. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like, which may be substituted or unsubstituted.

"Aryl," as used herein, refers to a monocyclic carbocyclic ring system or a bicyclic carbocyclic fused ring system having one or more aromatic rings. Representative examples of aryl include pyridyl, azulenyl, indanyl, indenyl, naphthyl, phenyl, tetrahydronaphthyl, and the like, which may in turn be substituted or unsubstituted.

"Acyl" is intended to mean a —C(O)—R group, where R is a suitable substituent such as H, alkyl or aryl, which may in turn be substituted or unsubstituted.

"Dipyrromethane" as used herein includes an unsubstituted or substituted dipyrromethane, which may be substituted one or more times at the 1, 2, 3, 5, 7, 8 or 9 positions with any suitable substituent such as halo, carbonyl, alkyl, fluoroalkyl including perfluoroalkyl, aryl (e.g., aryl at the 5 position; alkyl at the 1 and/or 9 position), fluoroaryl including perfluoroaryl, etc. Dipyrromethanes may be coupled to porphyrinic macrocycles at any suitable position on the dipyrromethanes, including the 1, 2, 3, 5, 7, 8, or 9 position.

"Hindered alkyl amine base" as used herein refers to an amine base containing bulky substituents, such as in triethylamine, diisopropylethylamine, and triphenylamine, and not as in propyl amine.

"Halo" as used herein refers to chloro, fluoro, bromo, or iodo.

"Active Ester" as used herein refers to a compound which may be used to acylate a dipyrromethane or 1-acyldipyrromethane. In general an active ester is a compound of the general formula RCOX, where X is a leaving group. Any suitable leaving group may be used, including but not limited to alkylthio, arylthio, acyloxy (i.e., $(RCO)_2O$), 2,4-dinitrophenyloxy, etc.

"Vilsmeier reagent" as used herein refers to a composition comprised of a dialkylamide and $POCl_3$. The dialkylamide may be of the general formula RC(=O)NR'R', where R is H, alkyl or aryl, and R' is alkyl, an example of such a dialkylamide being N-acylmorpholide.

"Anion leaving group" as used herein may be any suitable anionic leaving group, including but not limited to Cl, Br, and OTF (or "triflate", $O_3SCF_3$).

"Grignard reagent" has its conventional meaning in the art and includes compounds of the general formula RMgX, where X is bromo, chloro, or iodo, preferably bromo, and R is alkyl or aryl, preferably ethyl, sec-butyl, or mesityl.

"Hindered Grignard reagent" refers to a Grignard reagent as described above in which R is a bulky group such as mesityl, or more generally a group of the formula:

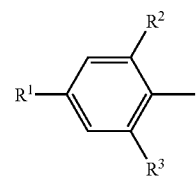

wherein $R^1$, $R^2$ and $R^3$ are each independently selected C1-C4 alkyl.

"Mukaiyama reagent" is described in further detail below.

"Eastern half" and "Western half" are as described in further detail below.

"Disilazane" as used herein refers to compounds of the formula:

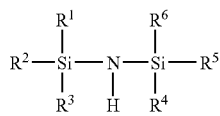

wherein $R^1$ through $R^6$ are each independently selected from the group consisting of alkyl (e.g., methyl, ethyl, propyl) and aryl (e.g., phenyl).

All United States Patent references cited herein are to be incorporated by reference herein in their entirety.

Starting material 1-monoacyldipyrromethanes. Starting materials for the methods described herein are generally prepared by acylating a dipyrromethane. As such the starting materials are typically provide in a crude form or mixture combined with other reaction reagents and products. Depending upon the end use planned for the product, the dipyrromethane may be substituted at the 5 position with H, alkyl, or aryl; or in other embodiments may be substituted at the 5 position with a substituent such as a dipyrromethane, porphyrin, dipyrrin, or diacyldipyrromethane (which substituent may be directly coupled at the 5 position or coupled by an intermediate linking group such as an alkyl or aryl group). Acylation of the dipyrromethane may be carried out in any of a variety of ways. In one embodiment, acylating carried out by reacting the dipyrromethane with a compound of the formula RCOX, where R is an organic substituent such as alkyl or aryl and X is halo, to form a mixed reaction product comprising a 1-monoacyldipyrromethane acylated at the 1 position with RCO—. In another embodiment, acylating is carried out by reacting the dipyrromethane with an acid chloride and a Grignard reagent to form the mixed reaction product comprising a 1-monoacyldipyrromethane. In another embodiment, acylating is carried out by reacting the dipyrromethane with an active ester to form the mixed reaction product comprising a 1-monoacyldipyrromethane. In another embodiment, acylating is carried out by reacting the dipyrromethane with a Vilsmeier reagent to form a mixed reaction product comprising a 1-monoacyldipyrromethane. See. e.g., D. Gryko et al., *J. Porphyrins Phthalocyanines* 7, 239-248 (2003).

Making 1-monoacyldipyrromethane metal complexes and separation of such complexes. As noted above, the present invention provides a method of making a metal complex, comprising: (a) providing a 1-monoacyldipyrromethane and then (b) combining (e.g., in a suitable solvent such as dichloromethane) said 1-monoacyldipyrromethane with a compound of the formula $R^1R^2MX$, wherein M is boron, $R^1$ and $R^2$ are each independently organic substituents (preferably substituents in which M is coupled by covalent link to a carbon atom in the organic substituents); and X is an anion leaving group; to produce a metal complex of the formula $DMR^1R^2$, wherein DH is said 1-monoacyldipyrromethane. Illustrative organic substituents for $R^1$ and $R^2$ are alkyl, alkenyl, alkynyl, and aryl, each of which can be unsubstituted or substituted one or more times with a substituent selected from the group consisting of alkyl, alkenyl, alkynyl, aryl, alkoxy, alkylcarbonyl, alkylcarbonyloxy, alkylsulfinyl, alkylsulfonyl, alkylthio, halo, cyano, nitro, sulfo, oxo, formyl, azido, and carbamoyl.

In some embodiments of the foregoing, the combining step is carried out by combining a mixture such as a crude reaction mixture containing the 1-monoacyldipyrromethane as a reaction product, along with other undesired compounds, with the compound of the formula $R^1R^2MX$. For example, the combining step may be carried out in a solution and said metal complex is solubilized or suspended in said solution, said method further comprising the steps of: (c) combining said metal complex with a hindered alkyl amine base in an organic solvent to form a solid (e.g., a crystal solid) comprising said metal complex; and then (d) separating the complex from the organic solvent by filtration, centrifugation, sedimentation, or any other suitable separation technique. The time and temperature of the combining step is not critical, but may for example be from 1 or 2 minutes to 24 hours in duration, and is most conveniently carried out for 10 minutes to two hours, at a temperature range of −20° C. to 50 or 100° C. or more (e.g., room temperature). Any suitable organic solvent may be used, including but not limited to methylene chloride, chloroform, 1,2-dichloroethane, toluene, chlorobenzene, etc.

In some embodiments the method further comprises the step of: (c) decomplexing said 1-monoacyldipyrromethane from said metal complex by combining the metal complex with an hydroxide, an alcohol, water, or combination thereof. Typical sources of hydroxide include but are not limited to KOH, NaOH, LiOH, $Ba(OH)_2$, $Mg(OH)_2$, etc. Typical alcohols include but are not limited to methanol, neopentyl glycol, ethanolamine, polyethylene glycol, 1,3-propanediol, pentaerythritol, and polyvinyl alcohol. Smooth decomplexation is obtained in refluxing solvents composed of water and tetrahydrofuran or alcohol and tetrahydrofuran. Decomplexation can be carried out in solution or with the hydroxy group that is coupled to (e.g., covalently coupled to) a solid support such as a solid support in accordance with known techniques.

In some embodiments, the compound of formula $R^1R^2MX$ may be immobilized on a such as a polymer support, where the groups R constitute a portion of the polymer or are otherwise coupled to the polymer (with immobilization on the solid support facilitating the subsequent separation of the acylated dipyrromethane product). Hence the method further comprises the step of: (c) releasing said 1-monoacyldipyrromethane complex from said solid support, which releasing may be carried out utilizing the decomplexing procedures described above.

Thus the present invention provides a 1-monoacyldipyrromethane-boron complex of the formula $DMR^1R^2$, wherein: DH is a 1-monoacyldipyrromethane, M is boron, and $R^1$ and $R^2$ are as described herein. The complex may be provided in solid form, including crystal solid form.

Direct synthesis of porphyrins. Among other things the present invention provides a method of making a porphyrin, comprising: providing a 1-monoacyldipyrromethane-boron complex as described herein, and then reducing said 1-monoacyldipyrromethane in the complex without prior decomplexation of said boron to produce said porphyrin. In some embodiments the reducing step is carried out with $NaBH_4$ in an organic solvent.

Making 1,9-diacyldipyrromethanes and porphyrins therefrom. A further aspect of the present invention is a method of making a 1,9-diacyldipyrromethane metal complex, comprising: providing a 1-monoacyldipyrromethane-boron complex as described herein; and then acylating said 1-monoacyldipyrromethane in said complex at the 9 position with a pyridyl thioate Mukaiyama reagent in the presence of a Grignard reagent and a base to produce said 1,9-diacyldipyrromethane metal complex. Preferably the conjugate acid of said base has a $pK_a$ greater than that of the conjugate acid of the nonacylated pyrrole group in said 1-monoacyldipyrromethane; thus the conjugate acid of the base typically has a pK$_a$ greater than 17. When the base is formed in situ (in which case at least a second equivalent of the Grignard reagent is typically required), the conjugate acid of the base preferably has a pK$_a$ less than that of the conjugate acid of the Grignard reagent (for example, a pK$_a$ less than 45). When the base is preformed and not formed in situ the pK$_a$ of the conjugate acid thereof may be greater, e.g., 50 or 60. The base may be the deprotonated form of a tetraalkylpiperidine (where said alkyl may be C1 to C4 alkyl, such as tetramethylpiperidine), dicycloalkylamine (where said alkyl may be C4 to C8 alkyl, such as dicyclohexylamine), or disilazane (as described above), accompanied by a cation such as K$^+$, Na$^+$, R$^+$, Cs$^+$, Ca$^{2+}$, Be$^{2+}$, Zn$^{2+}$, Al$^{3+}$, etc., preferably Li$^+$ and Mg$^{2+}$, most preferably Mg$^{2+}$. Preferred bases are compounds of the formula XMZ, where X is a disilazane as described above in deprotonated form, M is a cation as described above, and Z if present is alkyl, halo, or other anion for charge balance. Suitable Grignard reagents are known in the art, are described above, and are also described in, among other references, U.S. Pat. Nos. 6,617,282, 6,608,212, 6,603,000 and 6,600.040. The Mukaiyama reagent is, in general, any suitable Mukaiyama reagent, typically a 2-S-pyridyl thioate. The reaction may be carried out in any suitable (preferably non-aqueous) organic solvent, such as an ethereal solvent such as tetrahydrofuran (THF), at a temperature of from −78° C. to 100° C. and any suitable pressure, and is preferably carried out at room temperature under ambient pressure.

Where no base is used for 9 acylation and 2 equivalents of ethyl magnesium bromide (Grignard reagent) is used (in which case one equivalent of the Grignard reagent serves as the base), the results are not so good. However, if two equivalents of a hindered Grignard reagent, such as mesityl-MgBr, are used, the 9-acylation results are excellent, regardless of whether a base such as a disilazane base is present. Evidently, mesityl-MgBr is a more hindered base than that formed with a disilazane, and provides even better results than the disilazane.

1,9-diacyldipyrromethanes produced in metal complexes as described above may in turn be reduced, while still within the metal complex, with a reducing agent (e.g. NaBH$_4$) to form a diol from the 1,9-diacyldipyrromethane in the complex, and the diol then condensing with a dipyrromethane in accordance with known techniques to form a porphyrin ring compound therefrom.

In some embodiments of the foregoing, the method further comprises the step of decomplexing the 1,9-diacyldipyrromethane from said metal complex by combining the metal complex with an hydroxide, an alcohol, water, or combination thereof in essentially the same manner as described above.

In some embodiments, the present invention further provides a method of making a metal complex (typically to aid in purifying the 1,9-diacyldipyrromethanes), comprising: reacting a 1,9-diacyldipyrromethane with a compound of the formula R$^1$R$^2$M'X'$_2$ in the presence of a base, where R$^1$ and R$^2$ are the same as given above, M' is Sn, Si, Ge or Pb (preferably Sn), and X' is halo (e.g., chloro, bromo, iodo), OAc (where OAc is acetate), acac (acetylacetonate) or OTf (where OTf is triflate), to form a metal complex of the general formula DM'R$^1$R$^2$, wherein DH$_2$ is the 1,9-diacyldipyrromethane. Suitable bases include but are not limited to triethylamine, tributylamine, N,N-diisopropylamine, 1,8-diazabicyclo[5.4.0]undec-7-ene (or "DBU"), 1,5-diazabicyclo[4.3.0]non-5-ene (or "DBN"), and 2,6-di-tert-butylpyridine. Again the compound of formula R$^1$R$^2$M'X'$_2$ may be free in the reaction solution or immobilized on a solid support such as a polymer support, where the groups R$^1$ and R$^2$ then constitute a portion of the polymer or are otherwise coupled to the polymer (with immobilization on the solid support facilitating the subsequent separation of the acylated dipyrromethane product).

Making chlorins. A farther aspect of the present invention is a method of making a compound useful as a chlorin eastern half, comprising: providing a 1-monoacyldipyrromethane-boron complex as described above, and then halogenating (e.g., brominating) said 1-monoacyldipyrromethane in said complex at the 9 position to produce a 1-acyl-9-bromodipyrromethane boron complex useful as a chlorin eastern half, or substituting the 1-monoacyldipyrromethane at the 9 position with alkoxy or acetoxy as described in U.S. Pat. No. 6,559,374. Any halogenating agent may be used, including but not limited to N-chlorosuccinimide, N-bromosuccinimide, N-iodosuccinimide, 1,3-dichloro-5,5-dimethylhydantoin, 1,3-dibromo-5,5-dimethylhydantoin, chlorine, bromine, and iodine. The reaction is preferably carried out at a temperature less than room temperature, most preferably 0 to −100° C., in any suitable solvent such as tetrahydrofuran, dioxane, diethyl ether or other ethereal solvents, but preferably THF. The method may then further comprise the steps of condensing said 1-acyl-9-halodipyrromethane boron complex (containing the eastern half) (particularly the reduction product, i.e., the carbinol, derived from the 1-acyl-9-substituted dipyrromethane boron complex) with a chlorin western half (typically in an organic solvent in the presence of an acid) to form a condensation product; and then oxidatively cyclizing said condensation product (typically in an organic solvent in the presence of a base, an oxidant and a metal salt) to produce a chlorin. The terms "Eastern half" and "Western half" are known in the art of chlorin chemistry; reactions for producing a chlorin from eastern and western halves are known in the art of chlorin chemistry, and can be carried out in accordance with known techniques or variations thereof which will be apparent to those skilled in the art given the present disclosure. See, e.g., U.S. Pat. No. 6,559,374 to Lindsey and Balasubramanian.

Utility. 1-Acyldipyrromethanes are essential intermediates in the synthesis of trans-A$_2$B$_2$, trans-AB$_2$C, cis-A$_2$B$_2$, cis-AB$_2$C, and ABCD porphyrins; diverse chlorins; A$_2$B, AB$_2$, and ABC corroles; and bilanes. The boron-complexation strategy provides a facile method for the isolation of a 1-acyldipyrromethane from the crude acylation mixture. The boron-complexation strategy can be used for the purification of a wide variety of 1-acyldipyrromethanes. The 1-acyldipyrromethane-boron complexes can be decomplexed to give the 1-acyldipyrromethanes in good to excellent yields. Alternatively, reduction of a 1-acyldipyrromethane-boron complex followed by self-condensation of the resulting dipyrromethane-carbinol affords the corresponding trans-A$_2$B$_2$ porphyrin. The ability to isolate and handle 1-acyldipyrromethanes as dialkylboron complexes should increase the scale of 1-acyldipyrromethane syntheses and facilitate the preparation of a wide variety of porphyrinic compounds.

1-Acyldipyrromethanes produced as described herein can be used as an intermediate for the production of a variety of useful compounds, such as 1,9-diacyldipyrromethanes, which are in turn useful for the production of compounds such as porphyrin ring compounds or porphyrinic macrocycles. The porphyrinic macrocycles are useful, among other things, for the production of polymers thereof which may be immobilized or coupled to a substrate and used as light harvesting rods, light harvesting arrays, and solar cells, as described for example in U.S. Pat. No. 6,407,330 to Lindsey et al. or U.S. Pat. No. 6,420,648 to Lindsey. Porphyrinic macrocycles are also useful immobilized to a substrate for making charge storage molecules and information storage devices containing the same. Such charge storage molecules and information storage devices are known and described in, for example, U.S. Pat. Nos. 6,208,553 to Gryko et al.; 6,381,169 to Bocian et al.; and 6,324,091 to Gryko et al. The porphyrinic macrocycle may comprise a member of a sandwich coordination compound in the information storage molecule, such as described in U.S. Pat. No. 6,212,093 to Li et al. or U.S. Pat. No. 6,451,942 to Li et al.

The present invention is explained in greater detail in the following non-limiting Examples.

EXAMPLES

The synthesis of a 1-acyldipyrromethane (2) is achieved by treatment of a dipyrromethane (1) with EtMgBr in THF at room temperature followed by addition of a pyridyl thioester (5) in THF at −78° C.[2] The product mixture consists of unreacted dipyrromethane (1), the 1-acyldipyrromethane (2), and pyridyl thioester and/or other byproducts (Scheme 1). A suitable complexation aid for application to such a mixture should meet several criteria, including at least some of the following: (1) afford reaction with diverse 1-acyldipyrromethanes, (2) resist complex formation with other species in the reaction mixture, particularly the dipyrromethane, (3) yield a crystalline solid, (4) exhibit sufficient stability for routine handling, and (5) undergo decomplexation under mild conditions to liberate the 1-acyldipyrromethane in pure form.

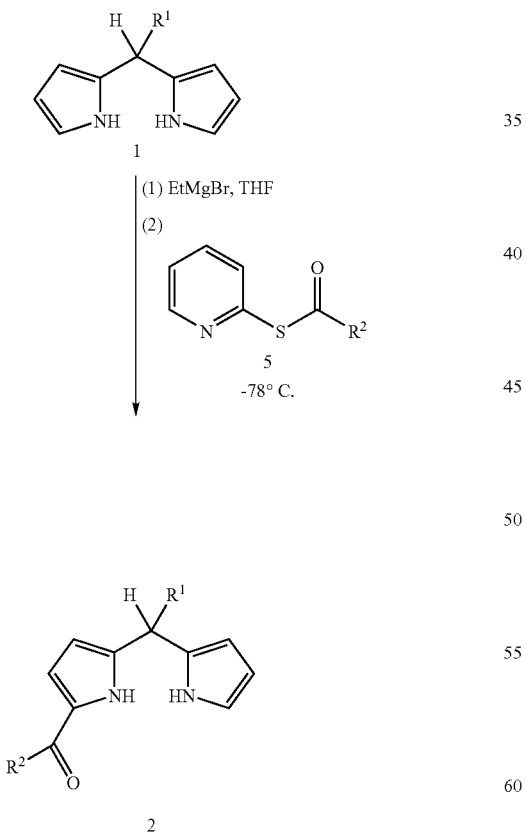

A number of metal complexes of 2-acylpyrroles are known, as shown in Chart 3. Pyrrole-2-carboxaldehyde forms a stable coordination complex (A) in conjunction with acetylacetone and copper(II), nickel(II), palladium(II), or platinum (II).[8] Pyrrole-2-carboxaldehyde and imino derivatives therefrom also form complexes with various metals or coordination centers (B,[9] C,[10] D,[11] E,[10] and F[12]). We began our search for suitable metal complexes of 1-acyldipyrromethanes on the basis of the known complexes of 2-acylpyrroles. Note that 1-acyldipyrromethanes and 2-acylpyrroles each contain the same α-acylpyrrole motif.

Chart 3

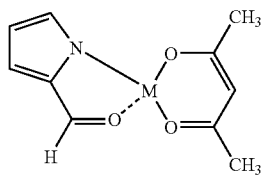

M = Ni, Cu, Pd, Pt

A:

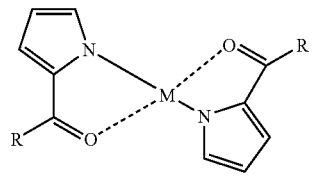

R = NMe₂, Me, H
M = Ge, Sn, Pb

B

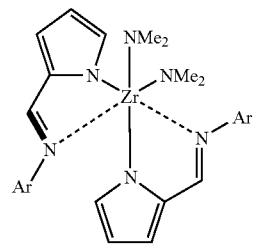

Ar = 2,6-di(i-Pr)phenyl

C

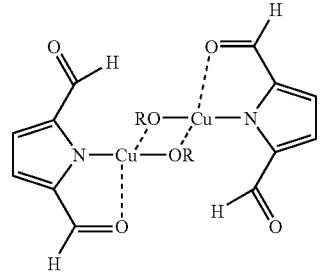

R = Me, Et

D:

-continued

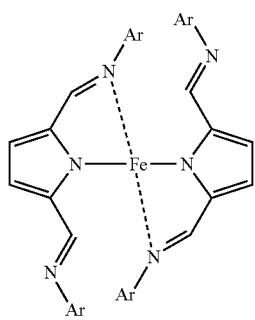

Ar = 2,6-di(i-Pr)phenyl

E

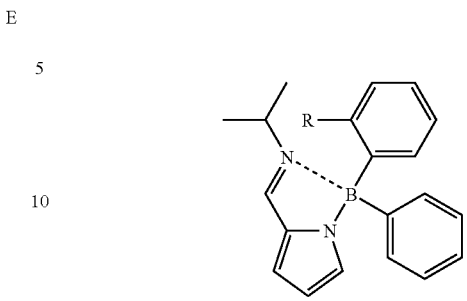

R = OMe

F

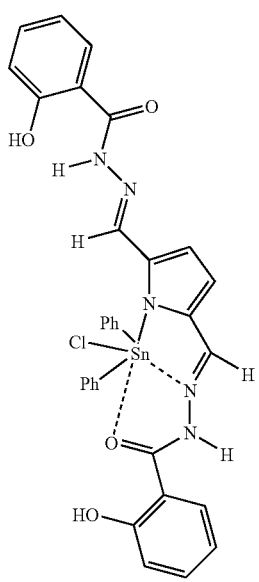

G

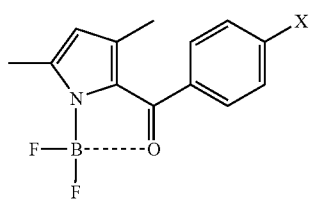

X = Br, I

H:

Results and Discussion

Identification of Suitable 1-Acyldipyrromethane-Coordination Complexes. A variety of metal reagents were examined as potential complexation aids for 1-acyldipyrromethanes. The metals include Mg(OAc)$_2$·4H$_2$O, Sc(OTf)$_3$, TiF$_4$, MnCl$_2$, Mn(OAc)$_2$, FeBr$_3$, Fe(OAc)$_2$, Fe(acac)$_3$, Co(OAc)$_2$·4H$_2$O, Ni(OAc)$_2$·4H$_2$O, Cu(OAc)$_2$·H$_2$O, Zn(OAc)$_2$·2H$_2$O, GeI$_4$, MoCl$_3$, RuCl$_3$·H$_2$O, Pd(OAc)$_2$, Pd(CH$_3$CN)$_2$Cl$_2$, Ag(OTf), CdCl$_2$, InCl$_3$, In(OAc)$_3$, SnF$_4$, SbCl$_5$, TeCl$_4$, CeI$_3$, EuCl$_3$, Dy(OTf)$_3$, Yb(OTf)$_3$, Tl(OAc), and BiCl$_3$. The conditions employed treatment of a methanolic solution of 2a[2] (100 mM) with the metal reagent (50 mM) at room temperature for 1 h. Most of the reagents examined gave multiple components. A readily isolable complex was obtained only with Cu(OAc)$_2$·H$_2$O, affording Cu-2a as a green precipitate (Scheme 2). While the formation of Cu-2a was promising, copper was found to have three limitations as a complexing agent: (1) the Cu-2a complex underwent decomplexation upon silica TLC; (2) formation of the complex was quite substrate selective: a copper complex was obtained for 1-p-toluoyl-5-phenyldipyrromethane (2a) but not with 1-pentafluorobenzoyl-5-(pentafluorophenyl)dipyrromethane (2e)[1]; and (3) the Cu-2a complex was an amorphous solid rather than a crystalline product.

Scheme 2

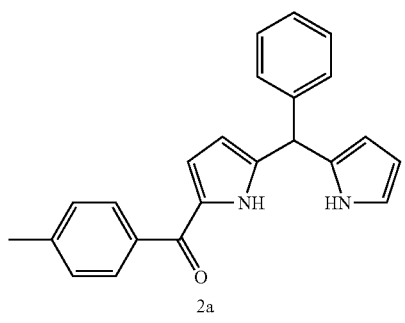

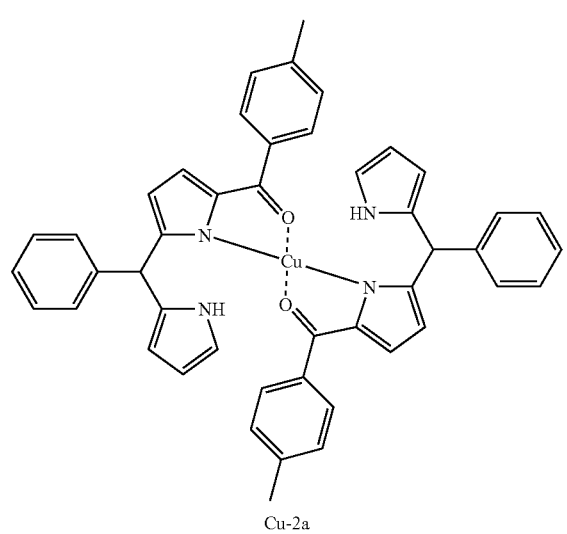

Cu-2a

Scheme 3

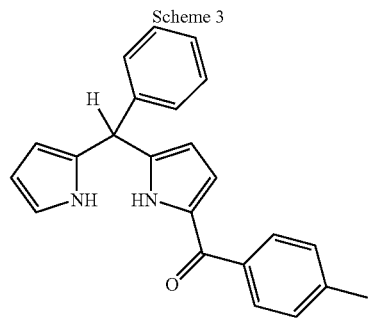

2a

R₂BX
TEA/CH₂Cl₂
rt, 1 h

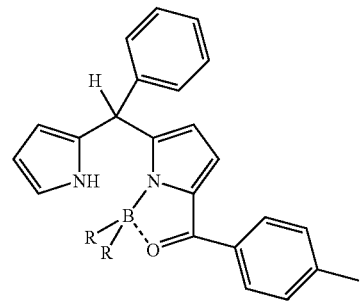

6a-BR₂

| R₂B | X | Complex | Yield |
|---|---|---|---|
| Bu₂B | OTf | 6a-BBu₂ | 93% |
| Me₂B | Br | 6a-BMe₂ | 91% |
| 9-BBN | OTf | 6a-BBN | 94% |
| F₂B | F | 6a-BF₂ | 0% |
| B-Catechol | Br | 6a-B(cat) | 0% |

9-BBN: 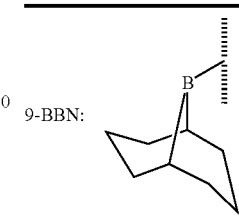

B-catechol: 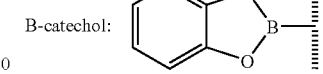

1-Acyldipyrromethane-Boron Complexes. To meet the objectives of broad applicability and formation of crystalline products, we turned to investigate boron complexes. The first boron derivative of a dipyrromethane species apparently was reported by Treibs et al.[13] who reacted BF₃-etherate with a dipyrrin to obtain a difluoroboron-dipyrrin complex. A wide variety of such difluoroboron-dipyrrin (BODIPY) derivatives have been prepared owing to their high fluorescence yields.[14] The boron-difluoride complexes of dipyrrins are exceptionally resistant to decomplexation.[13-15] 2-Ketopyrroles are also known to form stable boron-difluoride complexes (G, Chart 3).[15] A dialkylboron complex of a 2-iminopyrrole also is known (H, Chart 3).[16] W ught that boron complexes with B,B-dialkyl substituents might afford the appropriate balance of stability and susceptibility to decomplexation for our studies. A variety of compounds containing N-(dialkylboryl)pyrrole[17-25] or N-(diarylboryl)pyrrole[26] motifs have been prepared. Thus, reaction of 2a and Bu₂B-OTf in CH₂Cl₂ containing TEA at room temperature afforded the corresponding boron complex 6a-BBu₂ in 93% yield (Scheme 3). The boron complex was readily isolated by passage through a pad of silica. The generality of the complexation of 1-acyldipyrromethane 2a with various boron reagents was examined. The complex of 2a with 9-BBN gave an orange-yellow solid whereas the boron complex with dibutyl or dimethyl substituents gave an orange oil. On the other hand, no complex was obtained with BF₃.O(Et)₂ or B-bromocatechol borane. Owing to the high yield and formation of a crystalline product, we primarily used 9-BBN complexes for further study.

The selectivity of boron complexation was examined next. Dipyrromethane 1a did not give a boron complex (TLC analysis). However, a trace amount of an oxidized derivative, tentatively assigned as dipyrrinato-boron complex 7, was observed. The reaction of 1,9-diacyldipyrromethane 3a[1] and Bu$_2$B-OTf in CH$_2$Cl$_2$ containing TEA at room temperature afforded the corresponding bis-boron complex 3a-(BBU$_2$)$_2$ (Scheme 4).

Scheme 4

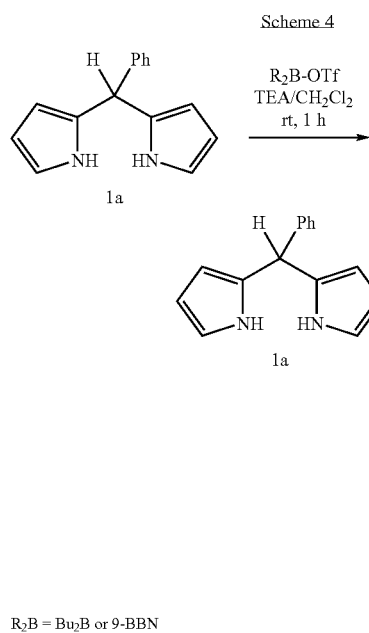

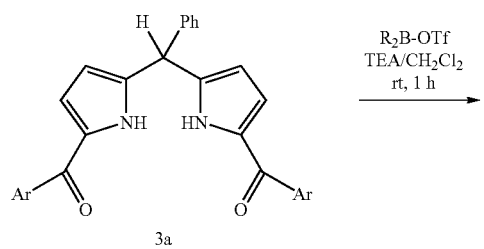

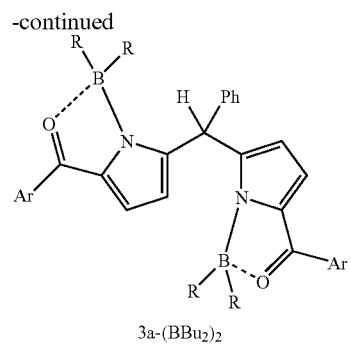

3a-(BBu$_2$)$_2$

Ar = 4-methylphenyl; R = Bu

The generality of the complexation with 9-BBN-OTf was examined with various 1-acyldipyrromethanes (Scheme 5). The requisite 1-acyldipyrromethanes 2a,[2] 2d,[7] 2e,[1] 2f,[2] 2g,[1] 2h,[7] and 2i[27] are known compounds while 2b and 2c were prepared herein following the general method.[2] In each case, the resulting boron complex was hydrophobic and easily isolated by passage through a pad of silica. The complexation of 1-acyldipyrromethanes 2a-2d and 2g with 9-BBN-OTf gave 6a-BBN-6d-BBN and 6g-BBN in excellent yields (87-97%). The reaction of 2e or 2f with 9-BBN-OTf gave complete reaction (TLC analysis), but partial decomplexation occurred upon passage through a silica pad, affording a mixture of 2e and 6e-BBN or 2f and 6f-BBN. The instability of the bulky, mesityl-substituted complex 6f-BBN was circumvented by reaction of 2f with Bu$_2$B-OTf, which gave 6f-BBu$_2$ as a stable product in 89% yield. The same approach with the pentafluorophenyl-substituted 2e gave 6e-BBu$_2$, which was isolated in pure form by silica pad separation but underwent facile decomplexation to 2e upon further handling.

Scheme 5

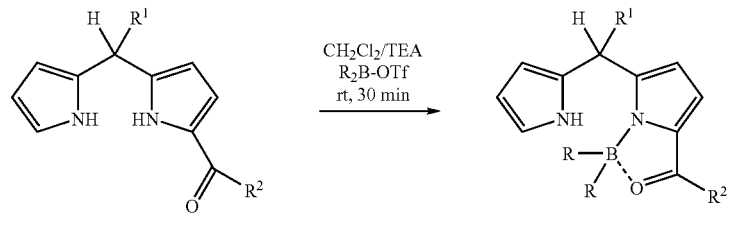

| 2 | R$^1$ | R$^2$ | R$_2$B | Product (Yield) |
|---|---|---|---|---|
| 2a | phenyl | 4-methylphenyl | 9-BBN | 6a-BBN (94%) |
| 2b | H | 4-methylphenyl | 9-BBN | 6b-BBN (91%) |

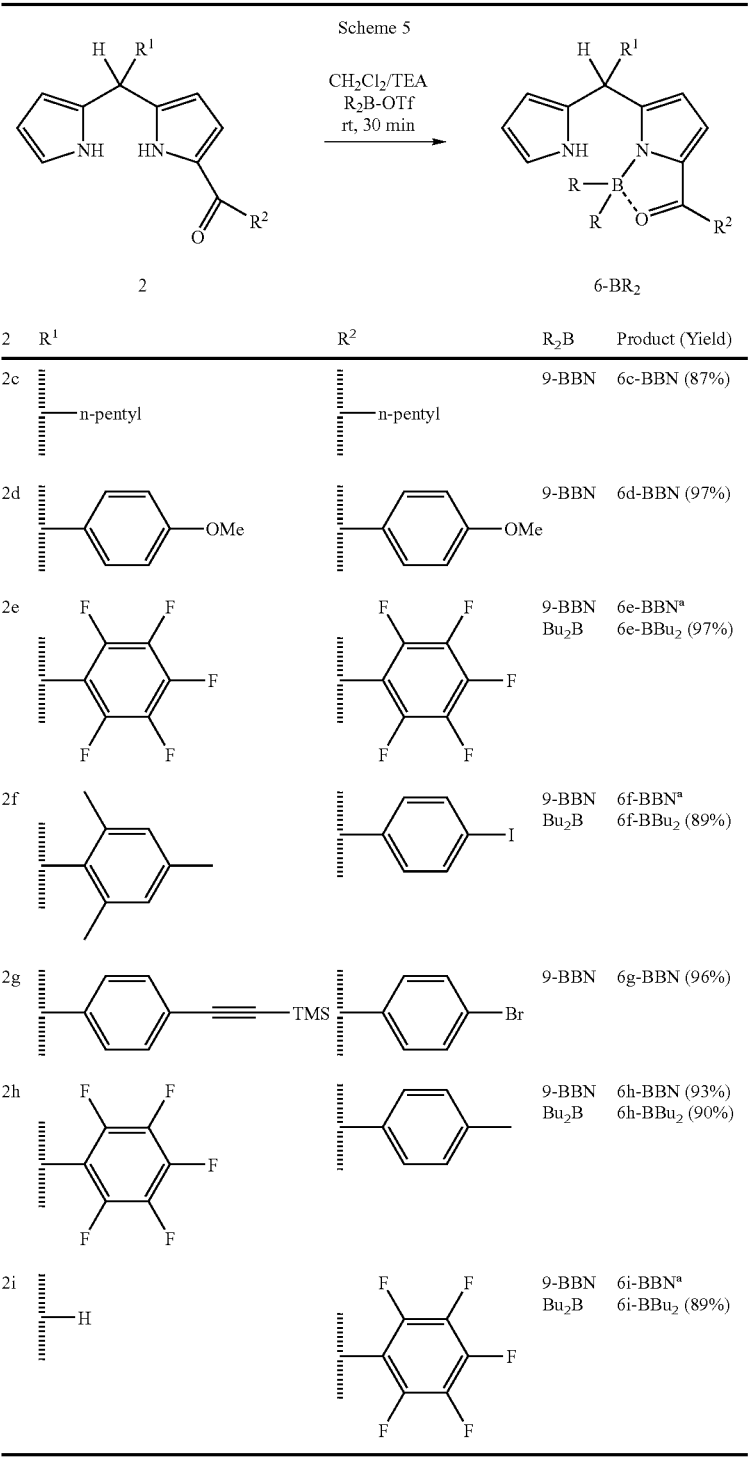

Scheme 5

<sup>a</sup>The product partially decomplexed upon chromatography.

To check the effect of the presence of a single pentafluorophenyl group at the 5- or 1-position, boron complexation reactions of 2h and 2i were investigated. The reaction of 2h (5-pentafluorophenyl substituent) with 9-BBN-OTf or Bu$_2$B-OTf gave a stable complex (6h-BBN or 6h-BBu$_2$) in excellent yield. However, reaction of 2i (1-pentafluorobenzoyl substituent) with 9-BBN-OTf gave a complex (6i-BBN) that proved unstable whereas the reaction of 2i with 9-BBu$_2$-OTf gave 6i-BBu$_2$ in 89% yield. Thus, the presence of the pentafluorophenyl group is deleterious only at the 1-acyl position.

It is noteworthy that almost all 9-BBN complexes of 1-acyldipyrromethanes were solids (the all-pentyl 6c-BBN was the one exception). On the other hand, almost all dibutylboron complexes of 1-acyldipyrromethanes were oils (6f-BBu$_2$ was the one exception). Regardless of state, the complexes are yellow-orange whereas the uncomplexed 1-acyldipyrromethanes are off-white solids. The 1-acyldipyrromethane-boron complexes are stable to water and routine handling. Unlike 1-acyldipyrromethanes, the 1-acyldipyrromethane-boron complexes can be precipitated/crystallized from CH$_2$Cl$_2$/hexanes, are relatively non-polar, and do not streak upon chromatography.

Characterization. The spectral changes upon boron complexation of a 1-acyldipyrromethane include the presence of the characteristic absorption at ~340-390 nm. The $^1$H NMR spectra show (1) disappearance of the NH resonance of the acylpyrrole unit, (2) a ~0.4 ppm upfield shift of the unsubstituted pyrrolic NH resonance, (3) a downfield shift of the meso-proton (~0.2 ppm), and (4) a downfield shift of the β-protons (~1 ppm) of the acylpyrrole. The $^{13}$C NMR spectra show the downfield shift of the carbonyl carbon (~8 ppm). The $^{11}$B NMR spectra of selected samples (6a-BBN-6d-BBN, and 6g-BBN) each showed a single peak at ~13 ppm, relative to the $^{11}$B standard, BF$_3$.O(Et)$_2$ (0 ppm). For comparison, the boron signal in the unacylated N-(9-borabicyclo[3.3.1]non-9-yl)pyrrole appears at 59.9 ppm.[23] The relative upfield shift of the acylated pyrrole is characteristic of organoboron species with coordination in the lone p orbital of the boron atom.[28] Elemental analyses for some of the boron complexes were satisfactory while others showed unsatisfactory results for carbon. This discrepancy may stem from solvent inclusion in the crystal lattice of the boron complexes. However, FABMS analyses of these complexes were satisfactory.

X-ray structural analysis was performed on 6a-BBN (FIG. 1). Complexation results in near coplanarity of the boron atom, α-carbonyl, and pyrrole unit. The C—O bond length (1.298 Å)[29] is longer than for that in 2-benzoylpyrrole (1.234 Å), suggesting some enolate character. At the same time, the C—C bond between the carbonyl carbon and the α-carbon of the acylpyrrole (1.402 Å) is significantly shorter than for that in 2-benzoylpyrrole (1.445 Å)[29] suggesting partial multiple bond character. Similar structural features were reported for the 2-ketopyrrole-BF$_2$ complex.[15]

Boron Complexation as a Purification Aid for 1-Acyldipyrromethanes. An integrated procedure consisting of 1-acylation and subsequent boron complexation was developed. The two steps are carried out as follows:

The dipyrromethane (1) is treated with 2.0 molar equiv of EtMgBr followed by 1.0 molar equiv of a Mukaiyama reagent[30] (5). The reaction mixture is quenched with aqueous NH$_4$Cl, and the organic layer is separated and concentrated, affording the crude product 2 (vide infra). Note that the use of boron complexation to isolate the 1-acyldipyrromethane enables use of a stoichiometric quantity of EtMgBr, rather than an excess as employed previously to ensure complete consumption of the Mukaiyama reagent.[2]

The residue (2) is dissolved in CH$_2$Cl$_2$ and treated with TEA and R$_2$B-OTf at room temperature for 1 h. Passage of the reaction mixture over a pad of silica using CH$_2$Cl$_2$/hexanes as eluant readily affords the boron complex.

In this manner, a series of dipyrromethanes (1a-f,[31] 1g[32]) was reacted with the appropriate Mukaiyama reagent (5a-e,[2] 5f[33]) followed by boron complexation with Bu$_2$B-OTf or 9-BBN-OTf. The boron complexes of 2a-2c and 2f-2h were readily obtained in good yield (Scheme 6).

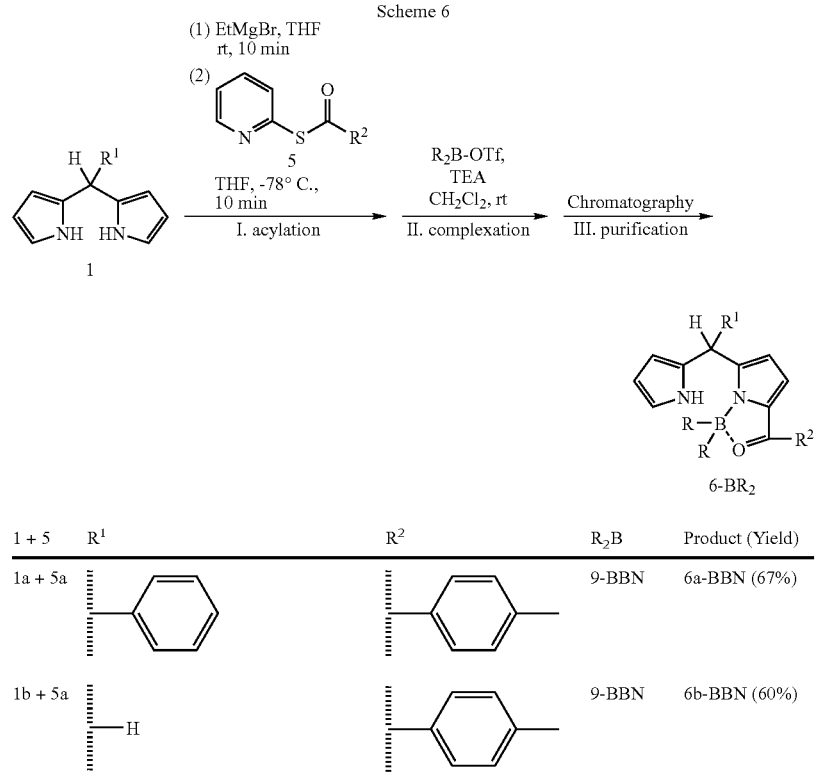

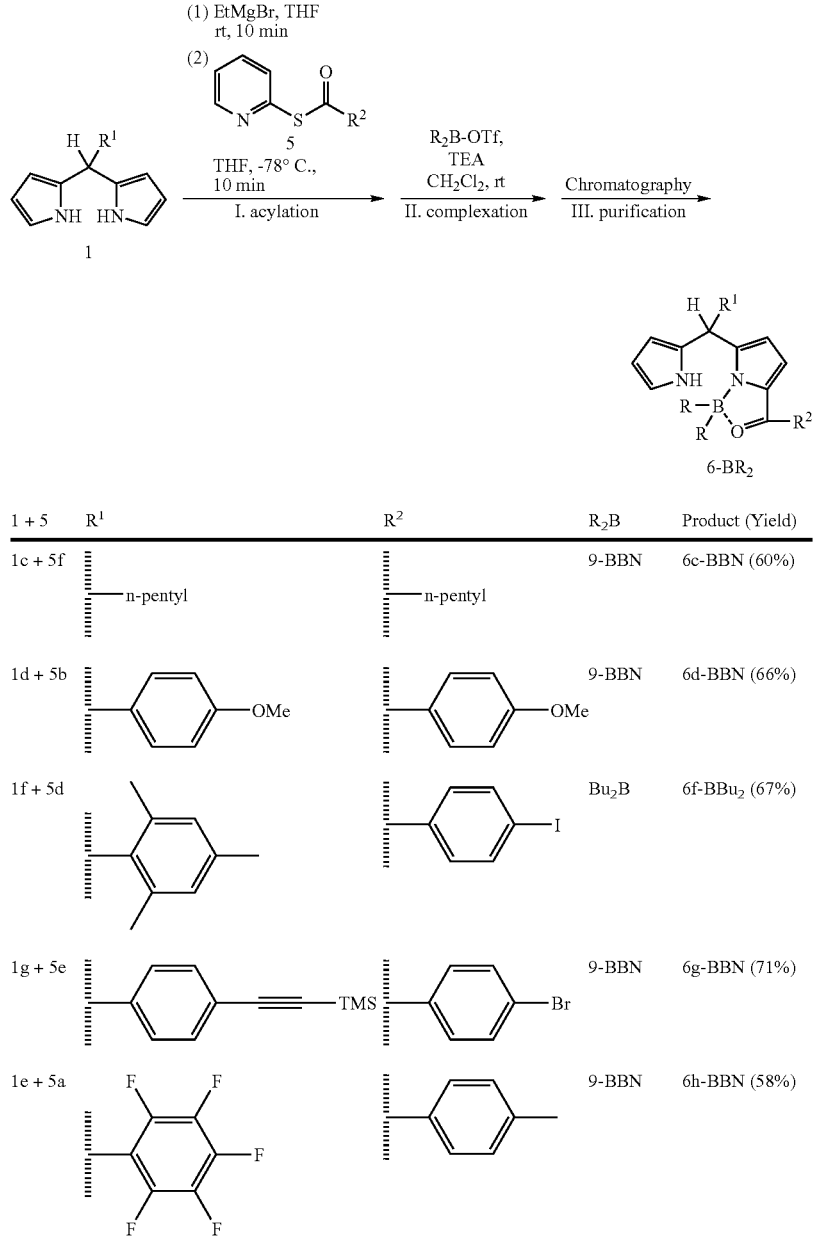

A slight modification to the general boron-complexation method was explored to further minimize use of chromatography. The modification entails use of a solvent for complexation that results in precipitation of the 1-acyldipyrromethane-boron complex. Thus, the reaction of 2a with 9-BBN-OTf in the presence of TEA in toluene afforded a precipitate, which largely consisted of 6a-BBN and the TfOH.TEA salt. Washing with water and methanol afforded the desired 1-acyldipyrromethane-boron complex 6a-BBN. This procedure was employed with 8.88 g of 2a, affording a precipitate (9.63 g, 52%) of analytically pure 6a-BBN. Silica pad separation of the filtrate afforded additional material (1.77 g), giving an overall yield of 62%. This procedure is well suited for synthesis at the multigram level. Note that no change in solvent was required for use with 2d; the boron complex 6d-BBN precipitated upon formation in $CH_2Cl_2$. Note that dipyrromethanes 1a-f were prepared by a streamlined procedure with minimal or no reliance on chromatography,[31] and 1g was prepared herein by the same procedure; accordingly, the overall route to form a 1-acyldipyrromethane can now be implemented with limited or no use of chromatography.

Decomplexation of 1-Acyldipyrromethane-Boron Complex. A simple method for decomplexation of the 1-acyldipyrromethane-boron complexes was investigated using 6a-BBN as a test case. The cleavage of the B—N bond in alkyl or aryl amines has been achieved with acids,[34,35] bases,[35] or ethanolamine.[35] The similar cleavage of N-(dialkylboron)pyrroles has been achieved with acids[19,24] or ethanol.[24] Given the potential lability of the 1-acyldipyrromethane to acidic conditions, we focused on neutral reaction conditions. Smooth decomplexation was obtained in refluxing solvents composed of $H_2O$/THF or ROH/THF, where ROH is methanol, neopentyl glycol, ethanolamine, polyethylene glycol, 1,3-propanediol, pentaerythritol or polyvinyl alcohol. In many cases, isolation could be achieved in nearly pure form without chromatography. A key factor in choice of alcohol is to avoid chromatography altogether for separation of the 1-acyldipyrromethane and the derivative formed upon reaction of ROH and the dibutylboron or 9-BBN species. We found that 1-pentanol generally afforded superior results. Accordingly, treatment of 6a-BBN with excess 1-pentanol in refluxing THF for 1 h followed by solvent removal, trituration with hot hexanes for 5 min, and recrystallization/precipitation from $CH_2Cl_2$/hexanes afforded 2a in 83% yield (Scheme 7).

Application of these decomplexation conditions to 6a-BBN, 6b-BBN, and 6d-BBN afforded 2a, 2b, and 2d, respectively in excellent yields (Scheme 7). The boron complex 6f-BBu$_2$ was decomplexed with neat 1-pentanol at 80° C. for 1 h followed by the workup procedure described above. Decomplexation of 6c-BBN with 1-pentanol in THF at reflux for 1 h afforded 2c, which was isolated upon passage through a pad of alumina.

Use of 1-Acyldipyrromethane-Boron Complexes in Porphyrin Formation. The reduction of a 1-acyldipyrromethane affords the corresponding dipyrromethane-1-carbinol, which upon self-condensation and oxidation affords the trans-$A_2B_2$ porphyrin.[2,33] The 1-acyldipyrromethane-boron complexes were examined as precursors to trans-$A_2B_2$ porphyrins, thereby avoiding the boron-decomplexation procedure. Thus, the boron complex 6a-BBu$_2$ was treated with NaBH$_4$ in THF/methanol for 40 min. TLC analysis indicated complete con-

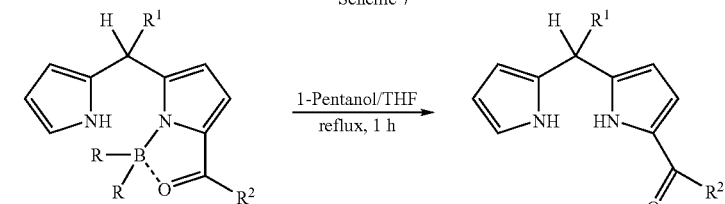

Scheme 7 sumption of 6a-BBu$_2$ and formation of a new polar spot. The reaction mixture was worked up in the standard way and the product was subjected to acid-catalyzed self-condensation [Yb(OTf)$_3$ in CH$_2$Cl$_2$][33] followed by oxidation with DDQ. Porphyrin 8 was obtained in 26% yield (Scheme 8). The boron complex 6a-BBN was treated similarly, affording porphyrin 8 in 17% yield. In both cases, no other porphyrin species were observed upon LD-MS[36] analysis of the crude reaction mixtures. For comparison, the reaction of the uncomplexed 1-acyldipyrromethane 2a affords porphyrin 8 in 25% yield.[33]

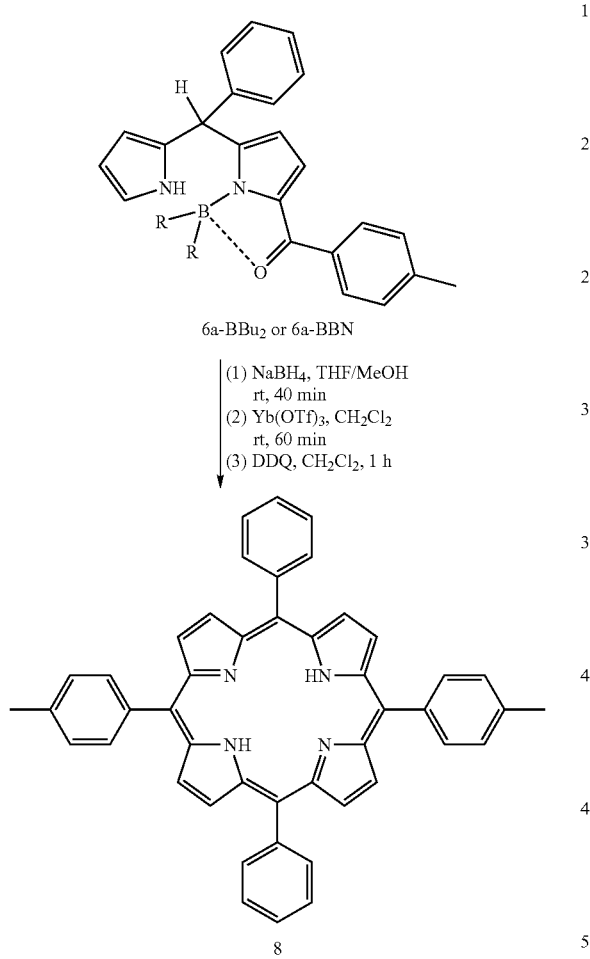

9-Acylation of 1-Acyldipyrromethane-Boron Complexes. The acylation of dipyrromethanes to form 1,9-diacyldipyrromethanes is an essential step in the rational synthesis of porphyrins. Dipyrromethanes with identical acyl groups at the 1- and 9-positions are key precursors to A$_3$B-, trans-A$_2$B$_2$-, and trans-AB$_2$C-porphyrins. Dipyrromethanes bearing two different acyl groups at the 1- and 9-positions are required precursors to cis-A$_2$B$_2$-, cis-A$_2$BC- and ABCD-porphyrins. Reaction of a 1-acyldipyrromethane (2) with EtMgBr and an acid chloride affords the 1,9-diacyldipyrromethane (3).[1] Other methods (Friedel-Crafts, Vilsmeier, benzoxathiolium salt) also have been examined for the 9-acylation of a 1-acyldipyrromethane.[7] Regardless of synthetic method, purification of acyldipyrromethane is difficult because acyldipyrromethanes (2 or 3) typically streak extensively upon chromatography and give amorphous powders upon attempted crystallization.

While the 1-acylation of dipyrromethanes proceeds well with yields of ~80-90%, the 9-acylation has proved more problematic and generally afforded yields of ≦60%. The difficulty with the second acylation, while puzzling, has led to use of a more potent acylating agent (e.g., an acid chloride) than the pyridyl thioate (Mukaiyama reagent)[37] employed for the 1-acylation. A more fundamental limitation stem from the requirement for the presence of a base to neutralize the HCl liberated upon acylation. In principle, 3 equiv of EtMgBr and 1 equiv of acid chloride are needed for the reaction, but in practice, 6 equiv of EtMgBr and 3 equiv of acid chloride are employed. Attempts to use various bases other than EtMgBr have generally afforded little improvement in the yield of the 1,9-diacyldipyrromethane.

Here we describe our studies on the use of 1-acyldipyrromethane-BR$_2$ complexes as acylation substrates. 9-BBN complexes were chosen because of their high crystallinity, however other dialkylboron complexes also can be used. We chose the reaction of 6a-BBN and S-2-pyridyl 4-methylbenzothioate (5a) as a model system for optimization of conditions. Thus, a solution of 6a-BBN (0.10 mmol, 1.0 M) in toluene at room temperature was treated with EtMgBr (0.15 mmol) followed by 5a (0.10 mmol, 1.0 M) in toluene (0.1 mL) (Scheme 9).

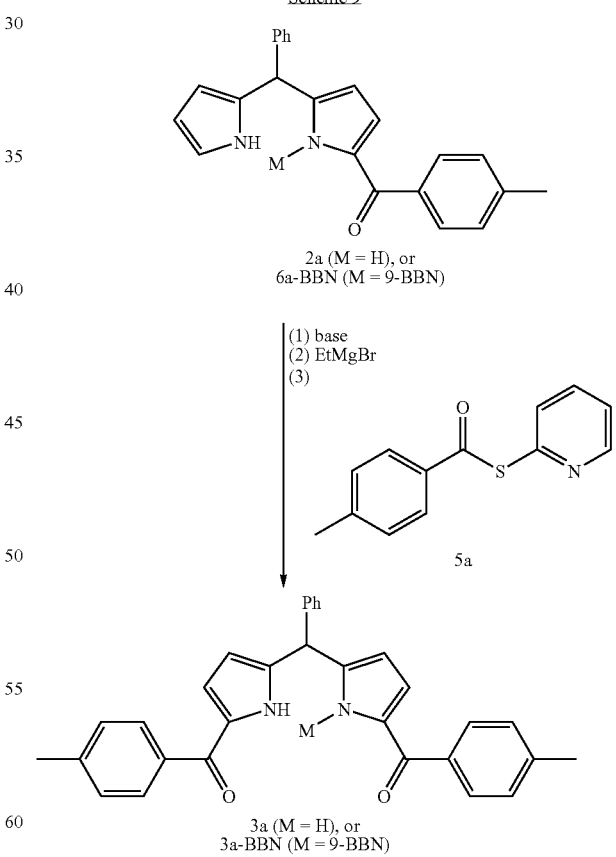

TLC and $^1$H NMR analysis indicated the presence of equal amounts (~1:1) of the desired 1,9-diacyldipyrromethane-BR$_2$ complex (3a-BBN) and the starting 1-acyldipyrromethane-BR$_2$ complex (6a-BBN) (entry 1, Table 1). The yield was determined by $^1$H NMR spectroscopic analysis of crude reaction samples by comparing the peak intensity for the H$^3$ proton signals for 1,9-diacylated (~6.46 ppm) and 1-acylated (~6.41 ppm) dipyrromethane-BR$_2$ complexes (Chart 4).

Chart 4

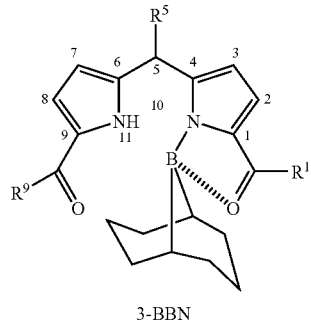

3-BBN

The use of THF rather than toluene as a solvent improved the relative yield of the 1,9-diacyldipyrromethane-BR$_2$ complex (~1.7:1.0; entry 2). Use of p-toluoyl chloride rather than the Mukaiyama reagent gave relatively little reaction (~0.4:1.0; entry 3). Use of 1 equiv of EtMgBr reduced the yield of the 1,9-diacyldipyrromethane-BR$_2$ complex (~1.1:1.0; entry 4). A limiting yield of 50% is expected considering that the liberated products (3a-BBN and pyridylthiol) are more acidic than the starting material (6a-BBN), causing decomposition of the 6a-BBN-MgBr complex. On the other hand, use of excess EtMgBr is expected to be ineffective owing to the competitive reaction of the Grignard reagent with Mukaiyama reagent (entry 5), forming the ketone. Indeed, the Mukaiyama reagents were initially developed for the synthesis of ketones.[37]

To overcome these problems we considered using a base whose conjugate acid (Base-H) has higher pK$_a$ than that of the liberated products (3a-BBN and pyridylthiol) and starting material 6a-BBN. Thus the requirement for the base strength is as follows Et-MgBr>Base-MgBr>pyrrole-MgBr>acylpyrrole-MgBr>pyridylthiolate-MgBr, where X-MgBr refers to the Grignard reagent formed from the conjugate base of the weak acid XH. In other words the conjugate acid of the base should have a pK$_a$ greater than that of pyrrole (~17.5) and less than that of ethane (~45). In addition the base should be non-nucleophilic. For such non-nucleophilic bases, we examined 2,2,6,6-tetramethylpiperidine (TMP), dicyclohexylamine and 1,1,1,3,3,3-hexamethyldisilazane (HMDS), which have pK$_a$ values[38] of 37, 36 and 26, respectively (entry 6-8). A significant improvement was obtained with use of 2,2,6,6-tetramethylpiperidine or dicyclohexylamine (~2:1; entries 6 and 7). Even greater improvement was obtained with HMDS, which gave a 4:1 ratio of 1,9-diacyl to 1-acyldipyrromethane products (entry 8).

A comparative study with an uncomplexed 1-acyldipyrromethane was performed using similar conditions with and without additional base. Thus, a solution of 1-(p-toluoyl)-5-phenyldipyrromethane (2a) (0.10 mmol) in THF (0.1 mL, 1.0 M) at room temperature was treated with EtMgBr (0.20 mmol) followed by 5a (0.10 mmol) in THF (0.1 mL, 1.0 M). TLC and $^1$H NMR analysis indicated the presence of the desired 1,9-diacyldipyrromethane (3a) and the starting 1-acyldipyrromethane (2a) in only a ~0.3:1 ratio (entry 9, Table 1). The ratio of 1,9-diacyldipyrromethane (3a) to the starting 1-acyldipyrromethane (2a) was improved slightly (~0.6:1) by treating 2a (0.10 mmol) in THF (0.1 mL) and HMDS (0.10 mmol) with EtMgBr (0.30 mmol) followed by addition of 5a (0.20 mmol) in THF (0.20 mL, 1.0 M) (entry 10, Table 1). While the addition of HMDS afforded an improvement in the yield, the presence of the non-nucleophilic buffering agent alone was insufficient to afford a high yield with the uncomplexed 1-acyldipyrromethane. The origin of the low yield of the reaction with the uncomplexed 1-acyldipyrromethane may stem from poor reactivity in an aggregate, or complexation of the two neighboring pyrrolic species in the 1-acyldipyrromethane. This procedure wherein a mixture of 1-acyldipyrromethane-BR$_2$ complex (6-BR$_2$) (1 equiv) and HMDS (1 equiv) is treated with EtMgBr (2 equiv) followed by addition of Mukaiyama reagent (5) (1 equiv) in

TABLE 1

Conditions for the 9-acylation of 1-acyldipyrromethanes

| Entry | Substrate (cmpd, mmol) | Solvent (mL) | Base (mmol) | EtMgBr[a] (mmol) | Temperature | RCOX[b] (mmol) | Product:Substrate[c] |
|---|---|---|---|---|---|---|---|
| 1 | 6a-BBN, 0.10 | Toluene (0.1) | — | 0.15 | RT | 0.10 | 1.0:1.0 |
| 2 | 6a-BBN, 0.10 | THF (0.1) | — | 0.15 | RT | 0.10 | 1.7:1.0 |
| 3 | 6a-BBN, 0.10 | THF (0.2) | — | 0.15 | RT | 0.11[d] | 0.4:1.0 |
| 4 | 6a-BBN, 0.10 | THF (0.1) | — | 0.10 | RT | 0.10 | 1.1:1.0 |
| 5 | 6a-BBN, 0.10 | THF (0.1) | — | 0.25 | RT | 0.10 | 1.0:1.0 |
| 6 | 6a-BBN, 0.10 | THF (0.2) | TMP (0.10) | 0.20 | 0° C. → RT | 0.10 | 2.1:1.0 |
| 7 | 6a-BBN, 0.10 | THF (0.2) | Dicyclohexylamine (0.10) | 0.20 | 0° C. → RT | 0.10 | 2.3:1.0 |
| 8 | 6a-BBN, 0.10 | THF (0.2) | HMDS (0.10) | 0.20 | 0° C. → RT | 0.10 | 4.0:1.0 |
| 9 | 2a, 0.10 | THF (0.10) | — | 0.20 | RT | 0.20 | 0.3:1.0 |
| 10 | 2a, 0.10 | THF (0.20) | HMDS (1.0) | 0.30 | 0° C. → RT | 0.20 | 0.6:1.0 |

[a]EtMgBr was used as a 1.0 M solution in THF.
[b]S-2-Pyridyl 4-methylbenzothioate (5a).
[c]The ratio was determined by $^1$H NMR spectroscopic analysis of crude reaction samples.
[d]p-Toluoyl chloride instead of 5a.

THF affords a superior yield of the corresponding 1,9-diacyl-dipyrromethane-BR$_2$ complex (3-BR$_2$). Moreover, the method enables use of the more gentle Mukaiyama reagents rather than acid chlorides for acylation.

On the basis of these observations we propose the following mechanism. The 1-acyldipyrromethane-BR$_2$ complex (6-BR$_2$) in principle requires only 1 equiv of EtMgBr owing to the absence of the NH (i.e. the protection afforded by the R$_2$B entity) to form the pyrrole-MgBr species. A second equiv of EtMgBr is used to make the non-nucleophilic buffering agent Base-MgBr, the Grignard derivative of the base. The pyrrole-MgBr species then reacts with the Mukaiyama reagent to give the acylpyrrolic-MgBr and pyridylthiol as a byproduct. Base-MgBr then reacts with pyridylthiol to give pyridylthiolate-MgBr and Base-H again. Note that like EtMgBr, Base-MgBr might also exist in a Schlenk equilibrium. Indeed, it is known that the Grignard derivative of HMDS exists in a multimeric complex.[39]

It is noteworthy that the requirement for the presence of a "buffering agent" is less onerous in the synthesis of acylpyrroles. Indeed, in Nicolaou's synthesis of 2-acylpyrroles using the pyrrolic Grignard reagent and a Mukaiyama reagent, six equivalents of the pyrrolic Grignard reagent were employed.[40] In those syntheses, the Mukaiyama reagent was the more valuable species. In the synthesis of 1,9-diacyldipyrromethanes, the 1-acyldipyrromethane is a valuable intermediate and not available in excess, but the Grignard reagent of HMDS provides a suitable buffering agent.

Use of 1,9-Diacyldipyrromethane-Boron Complexes for Porphyrin Formation. The 1,9-diacyldipyrromethane-boron complex 3a-BBN was examined as a precursor in a porphyrin-forming reaction. Thus, the boron complex 3a-BBN was treated with NaBH$_4$ in THF/methanol for 40 min. The reaction mixture was worked up in the standard way[1,2] and the product was subjected to acid-catalyzed condensation with dipyrromethane 1a followed by oxidation with DDQ. The corresponding porphyrin 8 was obtained in 20% yield. No other porphyrin species were observed upon LD-MS analysis of the crude reaction mixture.

Bromination of a 1-Acyldipyrromethane-Boron Complex. 1-Bromo-9-acyldipyrromethanes are precursors for the synthesis of chlorin building blocks.[4] A 1-bromo-9-acyldipyrromethane is prepared by bromination of a 1-acyldipyrromethane. Treatment of 6a-BBN with NBS in THF at −78° C. for 1 h afforded the desired 1-bromo-9-acyldipyrromethane as the 9-BBN complex 9a-BBN in 94% yield (Scheme 10).

Scheme 10

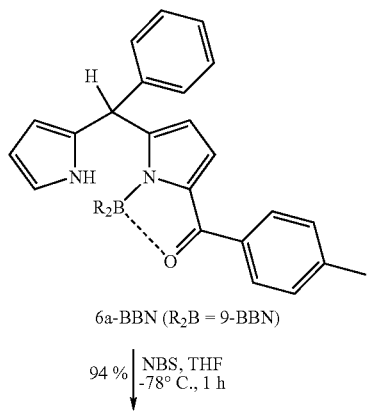

6a-BBN (R$_2$B = 9-BBN)

94% | NBS, THF
     | −78° C., 1 h

-continued

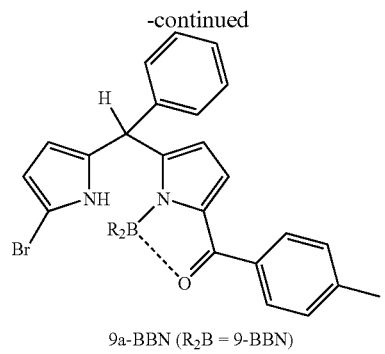

9a-BBN (R$_2$B = 9-BBN)

Experimental Section:

Noncommercial Compounds: Dipyrromethanes 1a-1f were prepared as described in the literature and analyzed for purity by gas chromatography.[31] 1-Acyldipyrromethanes 2a,[2] 2d,[7] 2e,[1] 2f,[2] 2g,[1] 2h,[7] 2i,[27] and 3a[1] and the Mukaiyama reagents 5a-5e,[2] and 5f[33] were prepared as described in the literature.

5-[4-(Trimethylsilylethynyl)phenyl]dipyrromethane (1g). Following a standard procedure,[31] a solution of 4-(trimethylsilylethynyl)benzaldehyde (7.00 g, 35.0 mmol) in pyrrole (347 mL) was degassed for 10 min. Then InCl$_3$ (1.11 g, 5.00 mmol) was added. The mixture was stirred at room temperature under argon. After 1.5 h, NaOH (6.00 g, 0.15 mol, 20-40 mesh beads) was added and the stirring was continued for an additional 45 min. The mixture was filtered and the filtrate was concentrated under high vacuum. The resulting oil was triturated with hexanes (50 mL), and the volatile components were evaporated. This procedure was repeated four times, affording a white solid. Crystallization from ethanol afforded off-white crystals (7.66 g, 69%): mp 122-123° C. (lit.[32] 120° C.); $^1$H NMR spectral data are consistent with reported values:[32] $^1$H NMR δ 0.26 (s, 9H), 5.45 (s, 1H), 5.88-5.92 (m, 2H), 6.13-6.19 (m, 2H), 6.67-6.71 (m, 2H), 7.14 (d, J=8.0 Hz, 2H), 7.42 (d, J=8.0 Hz, 2H), 7.83-7.90 (br, 2H); Anal. Calcd for C$_{18}$H$_{20}$N$_2$: C, 75.42; H, 6.96; N, 8.80. Found: C, 75.40; H, 6.88; N, 8.75.

1-(4-Methylbenzoyl)dipyrromethane (2b). Following a standard procedure[2] (but with a 500 mM solution of 1b rather than 1 M owing to limited solubility), a solution of 1b (0.731 g, 5.00 mmol) in THF (10 mL) at room temperature under argon was treated with EtMgBr (12.5 mL, 12.5 mmol, 1.0 M solution in THF) for 10 min. The solution was cooled to −78° C. Then a solution of 5a (1.15 g, 5.00 mmol) in THF (5.0 mL) was added. The reaction mixture was stirred at −78° C. for 10 min and at room temperature for 20 min. Standard workup and chromatography [silica, CH$_2$Cl$_2$/ethyl acetate (9:1)] afforded a pale brown solid (0.812 g, 62%): mp 172-174° C.; $^1$H NMR δ 2.43 (s, 3H), 4.09 (s, 2H), 6.03-6.06 (m, 1H), 6.08-6.12 (m, 1H), 6.14-6.18 (m, 1H), 6.51-6.55 (m, 1H), 6.80-6.86 (m, 1H), 7.27 (d, J=8.0 Hz, 2H), 7.76 (d, J=8.0 Hz, 2H), 9.25-9.28 (br, 1H), 10.94-10.98 (br, 1H); $^{13}$C NMR δ 21.8, 26.8, 106.4, 108.3, 110.3, 117.7, 123.1, 128.2, 129.3, 130.7, 136.0, 141.2, 142.7, 185.6; Anal. calcd for C$_{17}$H$_{16}$N$_2$O: C, 77.25; H, 6.10; N, 10.60. Found: C, 76.52; H, 5.89; N, 10.33.

1-Hexanoyl-5-pentyldipyrromethane (2c). Following a standard procedure,[2] a solution of 1c (1.08 g, 5.00 mmol) in THF (5.0 mL) under argon at room temperature was treated with EtMgBr (12.5 mL, 12.5 mmol, 1.0 M solution in THF) for 10 min. The solution was cooled to −78° C. Then a solution of 5f (1.05 g, 5.00 mmol) in THF (5.0 mL) was added. The reaction mixture was stirred at −78° C. for 10 min and at room temperature for 20 min. Standard workup and chromatography [silica, $CH_2Cl_2$/ethyl acetate (9:1)] afforded a light yellow oil (0.986 g, 63%): $^1H$ NMR δ 0.81-0.90 (m, 6H), 1.22-1.37 (m, 10H), 1.68-1.76 (m, 2H), 2.00-2.06 (m, 2H), 2.74 (t, J=7.6 Hz, 2H), 4.05 (t, J=7.6 Hz, 1H), 6.02-6.06 (m, 1H), 6.08-6.14 (m, 2H), 6.64-6.68 (m, 1H), 6.88-6.91 (m, 1H), 8.94-8.98 (br, 1H), 10.16-10.20 (br, 1H); $^{13}C$ NMR δ 14.1, 14.2, 22.7, 26.2, 27.7, 31.85, 31.87, 33.8, 38.1, 38.3, 105.0, 108.1, 108.5, 117.3, 119.5, 131.1, 133.0, 144.8, 191.9; Anal. calcd for $C_{20}H_{30}N_2O$: C, 76.39; H, 9.62; N, 8.91. Found: C, 76.15; H, 9.80; N, 8.77.

Screening Protocol for Metal Complexation of 1-Acyl-dipyrromethanes. A solution of 2a (0.017 g, 0.050 mmol) in methanol (0.5 mL) was treated with a solution of a metal reagent (0.025 mmol) in methanol (0.5 mL). The mixture was stirred at room temperature for 1 h. The reaction was monitored visually for precipitate formation. The reaction mixture was examined by TLC (silica, $CH_2Cl_2$/ethyl acetate, 9:1) and by absorption spectroscopy.

Bis [1-(4-methylbenzoyl)-5-phenyldipyrromethan-10-yl] copper(II) (Cu-2a). A solution of 2a (0.25 mmol, 85 mg) in methanol (2.5 mL) was treated with a warm solution of $Cu(OAc)_2 \cdot H_2O$ (0.30 mmol, 26 mg) in methanol (1 mL). The mixture was stirred at room temperature for 20 min. The resulting precipitate was filtered. The filtered material was washed with methanol and dried in vacuo to afford a green powder (75 mg, 81%): Anal. calcd for $C_{46}H_{38}CuN_4O_2$: C, 74.42; H, 5.16; N, 7.55. Found: C, 73.93; H, 5.22; N, 7.40; $\lambda_{abs}$ 380 nm.

10-(Dibutylboryl)-1-(4-methylbenzoyl)-5-phenyldipyr-romethane ($6a$-$BBU_2$). A solution of 2a (0.340 g, 1.00 mmol) in $CH_2Cl_2$ (2 mL) was treated with TEA (0.335 mL, 2.40 mmol) followed by $Bu_2B$-OTf (2.00 mL, 2.00 mmol, 1.0 M in $CH_2Cl_2$). After 30 min, the mixture was passed through a pad of silica (4×8 cm) eluting with $CH_2Cl_2$. The product eluted as a fast-moving yellow band, which upon concentration afforded an orange oil (0.431 g, 93%): $^1H$ NMR δ 0.36-0.52 (m, 2H), 0.61 (t, J=7.2 Hz, 3H), 0.65-1.18 (m, 13H), 2.47 (s, 3H), 5.60 (s, 1H), 5.85-5.88 (m, 1H), 6.13-6.17 (m, 1H), 6.45 (d, J=4.0 Hz, 1H), 6.68-6.72 (m, 1H), 7.20-7.38 (m, 8H), 7.79-7.83 (br, 1H), 8.11 (d, J=8.0 Hz, 2H); $^{13}C$ NMR δ 14.3, 14.4, 22.2, 22.6, 22.7, 26.17, 26.24, 27.1, 27.5, 44.2, 107.9, 108.8, 117.4, 117.8, 119.3, 127.3, 128.0, 128.77, 128.83, 129.98, 130.01, 132.2, 134.2, 141.5, 145.4, 150.1, 176.5; FABMS obsd 465.3074 [(M+H)$^+$], calcd 465.3077 ($C_{31}H_{37}BN_2O$); Anal. calcd for $C_{31}H_{37}BN_2O$: C, 80.17; H, 8.03; N, 6.03. Found: C, 79.98; H, 8.06; N, 5.95; $\lambda_{abs}$ 393 mm.

10-(Dimethylboryl)-1-(4-methylbenzoyl)-5-phenyldipyr-romethane ($6a$-$BMu_2$). A solution of 2a (0.340 g, 1.00 mmol) in $CH_2Cl_2$ (2 mL) was treated with TEA (0.335 mL, 2.40 mmol) followed by $Me_2B$—Br (0.390 mL, 1.00 mmol). After 30 min, the mixture was passed through a pad of silica (4×8 cm) eluting with $CH_2Cl_2$. The product eluted as a fast-moving yellow band, which upon concentration afforded an orange oil (0.344 g, 91%): $^1H$ NMR δ 0.04 (s, 3H), 0.15 (s, 3H), 2.48 (s, 3H), 5.66 (s, 1H), 5.87-5.92 (m, 1H), 6.15-6.19 (m, 1H), 6.43 (d, J=4.0 Hz, 1H), 6.70-6.75 (m, 1H), 7.24-7.38 (m, 8H), 7.84-7.88 (br, 1H), 8.11 (d, J=8.0 Hz, 2H); $^{13}C$ NMR δ 6.8, 22.1, 44.1, 107.9, 108.6, 117.5, 118.3, 119.3, 127.3, 128.1, 128.8, 128.9, 129.95, 129.99, 132.0, 133.1, 141.4, 145.5, 150.1, 176.1; FABMS obsd 381.2158 [(M+H)$^+$], calcd 381.2138 ($C_{25}H_{25}BN_2O$); Anal. calcd for $C_{25}H_{25}BN_2O$: C, 78.96; H, 6.63; N, 7.37. Found: C, 78.66; H, 6.60; N, 7.28; $\lambda_{abs}$ 393 nm.

10-(9-Borabicyclo[3.3.1]non-9-yl)-1-(4-methylbenzoyl)-5-phenyldipyrromethane (6a-BBN). A solution of 2a (0.680 g, 2.00 mmol) in $CH_2Cl_2$ (4 mL) was treated with TEA (0.670 mL, 4.80 mmol) followed by 9-BBN-OTf (8.00 mL, 4.00 mmol, 0.5 M in hexanes). After 30 min, the mixture was passed through a pad of silica (4×8 cm) eluting with $CH_2Cl_2$. The product eluted as a fast-moving yellow band, which upon concentration afforded a yellow-orange solid (0.863 g, 94%): mp 187° C. (dec.); $^1H$ NMR δ 0.66-0.71 (m, 2H), 1.65-1.84 (m, 6H), 1.95-2.25 (m, 6H), 2.48 (s, 3H), 5.83-5.86 (m, 1H), 6.01 (s, 1H), 6.13-6.17 (m, 1H), 6.41 (d, J=4.0 Hz, 1H), 6.69-6.73 (m, 1H), 7.18 (d, J=8.0 Hz, 2H), 7.22-7.38 (m, 6H), 7.83-7.87 (br, 1H), 8.11 (d, J=8.0 Hz, 2H); $^{13}C$ NMR δ 22.0, 23.8, 25.1, 25.9, 26.4, 30.5, 30.8, 34.48, 34.54, 44.7, 108.1, 108.5, 117.4, 118.2, 120.8, 127.0, 128.1, 128.4, 128.6, 129.7, 129.9, 132.3, 134.8, 142.1, 145.0, 151.9, 174.4; $^{11}B$ NMR δ 12.34; FABMS obsd 460.2674 [M$^+$], calcd 460.2686 ($C_{31}H_{33}BN_2O$); Anal. calcd for $C_{31}H_{33}BN_2O$: C, 80.87; H, 7.22; N, 6.08. Found: C, 78.96; H, 7.13; N, 5.85; $\lambda_{abs}$ 381 nm.

10-(9-Borabicyclo[3.3.1]non-9-yl)-1-(4-methylbenzoyl) dipyrromethane (6b-BBN). Following the procedure for 6a-BBN, reaction of 2b (0.529 g, 2.00 mmol) afforded a yellow-orange solid (0.696 g, 91%): mp 147° C. (dec.); $^1H$ NMR δ 0.71-0.78 (m, 2H), 1.67-1.75 (m, 4H), 1.76-1.91 (m, 4H), 1.98-2.14 (m, 2H), 2.16-2.26 (m, 2H), 2.48 (s, 3H), 4.34 (s, 2H), 6.03-6.06 (m, 1H), 6.16-6.18 (m, 1H), 6.36 (d, J=4.0 Hz, 1H), 6.69-6.72 (m, 1H), 7.29 (d, J=4.0 Hz, 1H), 7.36 (d, J=8.0 Hz, 2H), 7.90-7.94 (br, 1H), 8.11 (d, J=8.0 Hz, 2H); $^{13}C$ NMR δ 22.1, 24.0, 25.2, 26.8, 29.5, 31.5, 34.5, 107.1, 108.7, 117.5, 118.3, 120.7, 128.2, 128.7, 129.8, 129.9, 135.3, 145.0, 149.5, 174.1; $^{11}B$ NMR δ 12.74; FABMS obsd 384.2395 [M$^+$], calcd 384.2373 ($C_{25}H_{29}BN_2O$); Anal. calcd for $C_{25}H_{29}BN_2O$: C, 78.13; H, 7.61; N, 7.29. Found: C, 78.17; H, 7.58; N, 7.09; $\lambda_{abs}$ 380 nm.

10-(9-Borabicyclo[3.3.1]non-9-yl)-1-hexanoyl-5-pentyl-dipyrromethane (6c-BBN). Following the procedure for 6a-BBN, reaction of 2c (0.529 g, 2.00 mmol) afforded an orange oil (0.758 g, 87%): $^1H$ NMR δ 0.55-0.64 (m, 2H), 0.82-0.94 (m, 6H), 1.19-1.54 (m, 12H), 1.62-1.91 (m, 8H), 1.96-2.17 (m, 6H), 2.81 (t, J=8.0 Hz, 2H), 4.43 (t, J=8.0 Hz, 1H), 6.03-6.06 (m, 1H), 6.13-6.17 (m, 1H), 6.39 (d, J=4.0 Hz, 1H), 6.62-6.67 (m, 1H), 7.05 (d, J=4.0 Hz, 1H), 7.76-7.80 (br, 1H); $^{13}C$ NMR δ 14.1, 14.2, 22.5, 22.6, 22.7, 24.0, 25.0, 25.8, 26.3, 27.6, 30.7, 30.8, 31.5, 31.7, 32.2, 34.19, 32.22, 36.4, 39.2, 105.2, 108.5, 117.0, 117.57, 117.63, 133.5, 136.5, 154.8, 184.3; $^{11}B$ NMR δ 13.22; FABMS obsd 434.3481 [M$^+$], calcd 434.3468 ($C_{28}H_{43}BN_2O$); Anal. calcd for $C_{28}H_{43}BN_2O$: C, 77.41; H, 9.98; N, 6.45. Found: C, 75.22; H, 9.90; N, 6.40; $\lambda_{abs}$ 345 nm.

10-(9-Borabicyclo[3.3.1]non-9-yl)-1-(4-methoxyben-zoyl)-5-(4-methoxyphenyl)dipyrromethane (6d-BBN). Following the procedure for 6a-BBN, reaction of 2d (0.773 g, 2.00 mmol) afforded a yellow-brown solid (0.986 g, 97%): mp 72-73° C.; $^1H$ NMR δ 0.64-0.74 (m, 2H), 1.62-1.86 (m, 6H), 1.98-2.24 (m, 6H), 3.79 (s, 3H), 3.92 (s, 3H), 5.82-5.87 (m, 1H), 5.96 (s, 1H), 6.12-6.17 (m, 1H), 6.40 (d, J=4.0 Hz, 1H), 6.69-6.72 (m, 1H), 6.84 (d, J=8.0 Hz, 2H), 7.05 (d, J=8.0 Hz, 2H), 7.10 (d, J=8.0 Hz, 2H), 7.30 (d, J=4.0 Hz, 1H), 7.84-7.88 (br, 1H), 8.21 (d, J=8.0 Hz, 2H); $^{13}C$ NMR δ 24.0, 25.2, 26.0, 26.5, 30.6, 30.9, 34.6, 34.7, 44.0, 55.4, 55.8, 107.9, 108.6, 114.0, 114.7, 117.4, 117.8, 120.5, 123.5, 129.6, 130.0, 133.0, 134.4, 134.5, 151.7, 158.6, 164.4, 173.8; $^{11}B$ NMR δ 12.69; FABMS obsd 506.2749 [M$^+$], calcd 506.2741 ($C_{32}H_{35}BN_2O_3$); Anal. calcd for $C_{32}H_{35}BN_2O_3$: C, 75.89; H, 6.97; N, 5.53. Found: C, 74.75; H, 7.37; N, 5.01; $\lambda_{abs}$ 388 nm.

10-(Dibutylboryl)-1-(pentafluorobenzoyl)-5-pentafluorophenyldipyrromethane (6e-BBu$_2$). Following the procedure for 6a-BBu$_2$, reaction of 2e (0.506 g, 1.00 mmol) afforded an orange oil (0.608 g, 97%): $^1$H NMR δ 0.13-0.35 (m, 2H), 0.58-1.39 (m, 16H), 5.94 (s, 1H), 6.00 (s, 1H), 6.15-6.20 (m, 1H), 6.61 (d, J=4.0 Hz, 1H), 6.74-6.80 (m, 1H), 7.04-7.10 (m, 1H), 8.05-8.09 (br, 1H); $^{13}$C NMR δ 14.1, 14.3, 20.9, 21.4, 26.0, 26.2, 26.9, 27.4, 33.5, 33.9, 108.5, 109.2, 109.4, 111.3, 118.8, 119.6, 119.7, 119.8, 122.1, 122.3, 127.0, 136.9 (m), 138.0, 139.6 (m), 142.1 (m), 142.9 (m), 143.9 (m), 144.4 (m), 145.5 (m), 146.4 (m), 147.0 (m), 150.6, 166.0. This compound partially decomplexed to 2e upon handling due to exposure to moisture.

10-(Dibutylboryl)-1-(4-iodobenzoyl)-5-mesityldipyrromethane (6f-BBu$_2$). Following the procedure for 6a-BBu$_2$, reaction of 2f (0.494 g, 1.00 mmol) afforded a yellow-orange solid (0.548 g, 89%): mp 53-54° C.; $^1$H NMR δ –0.25--0.17 (m, 1H), 0.24-0.39 (m, 2H), 0.55-0.98 (m, 13H), 1.14-1.27 (m, 2H), 2.15 (s, 6H), 2.62 (s, 3H), 5.88 (s, 1H), 5.90-5.93 (m, 1H), 6.16-6.20 (m, 1H), 6.50 (d, J=4.0 Hz, 1H), 6.66-6.70 (m, 1H), 6.83 (s, 2H), 7.17 (d, J=4.0 Hz, 1H), 7.80-7.84 (br, 1H), 7.85-7.94 (m, 4H); $^{13}$C NMR δ 14.3, 14.5, 20.9, 21.2, 21.8, 26.1, 26.2, 27.3, 27.5, 40.1, 101.9, 108.0, 108.9, 116.8, 117.0, 122.8, 130.0, 130.1, 130.6, 130.9, 134.8, 135.3, 136.9, 137.2, 138.6, 153.0, 174.7; FABMS obsd 619.2390 [(M+H)$^+$], calcd 619.2357 (C$_{33}$H$_{40}$BIN$_2$O); Anal. calcd for C$_{33}$H$_{40}$BIN$_2$O: C, 64.09; H, 6.52; N, 4.53. Found: C, 64.08; H, 6.62; N, 4.40; λ$_{abs}$ 404 nm.

10-(9-Borabicyclo[3.3.1]non-9-yl)-1-(4-bromophenyl)-5-[4-(2-trimethylsilyl)ethynylphenyl]dipyrromethane (6g-BBN). Following the procedure for 6a-BBN, reaction of 2g (0.529 g, 2.00 mmol) afforded a yellow-orange solid (1.19 g, 96%): mp 172° C. (dec.); $^1$H NMR δ 0.24 (s, 9H), 0.64-0.73 (m, 2H), 1.64-1.85 (m, 6H), 1.94-2.09 (m, 4H), 2.12-2.24 (m, 2H), 5.83 (s, 1H), 6.00 (s, 1H), 6.13-6.18 (m, 1H), 6.39 (d, J=4.0 Hz, 1H), 6.71-6.75 (m, 1H), 7.09 (d, J=8.0 Hz, 2H), 7.32 (d, J=4.0 Hz, 1H), 7.40 (d, J=8.0 Hz, 2H), 7.68-7.74 (m, 2H), 7.82-7.86 (br, 1H), 8.02-8.10 (m, 2H); $^{13}$C NMR δ 0.18, 23.8, 25.1, 25.9, 26.6, 30.7, 30.8, 34.6, 44.8, 94.7, 104.9, 108.4, 108.8, 117.9, 118.7, 121.6, 122.1, 128.4, 129.2, 129.7, 131.0, 131.7, 132.4, 132.6, 132.7, 135.1, 142.4, 152.5, 173.2; $^{11}$B NMR δ 13.98; FABMS obsd 620.2057 [M$^+$], calcd 620.2030 (C$_{35}$H$_{38}$BBrN$_2$OSi); Anal. calcd for C$_{35}$H$_{38}$BBrN$_2$OSi: C, 67.64; H, 6.16; N, 4.51. Found: C, 67.41; H, 6.26; N, 4.43; λ$_{abs}$ 388 nm.

10-(9-Borabicyclo[3.3.1]non-9-yl)-1-(4-methylbenzoyl)-5-(pentafluorophenyl)dipyrromethane (6h-BBN). Following the procedure for 6a-BBN, reaction of 2h (0.430 g, 1.00 mmol) afforded a yellow-orange solid (0.512 g, 93%): mp 154-156° C. (dec.); $^1$H NMR δ 0.58-0.64 (m, 1H), 0.68-0.74 (m, 1H), 1.58-1.85 (m, 6H), 1.94-2.24 (m, 6H), 2.50 (s, 3H), 5.79 (s, 1H), 6.12-6.18 (m, 1H), 6.30 (s, 1H), 6.60 (d, J=4.0 Hz, 1H), 6.62-6.68 (m, 1H), 7.38 (d, J=4.0 Hz, 1H), 7.39 (d, J=8.0 Hz, 2H), 7.75-7.78 (br, 1H), 8.15 (d, J=8.0 Hz, 2H); $^{13}$C NMR δ 22.2, 23.9, 25.1, 26.3, 27.2, 29.8, 31.3, 34.67, 34.71, 36.3, 106.9, 109.2, 117.4, 118.3, 120.56, 120.60, 120.64, 127.9, 129.6, 130.07, 130.14, 135.9, 136.8 (m), 139.4 (m), 142.0 (m), 144.4 (m), 145.8, 146.4, 146.9 (m), 175.9; FABMS obsd 550.2229 [M$^+$], calcd 550.2215 (C$_{31}$H$_{28}$BF$_5$N$_2$O); Anal. calcd for C$_{31}$H$_{28}$BF$_5$N$_2$O: C, 67.65; H, 5.13; N, 5.09. Found: C, 68.05; H, 5.23; N, 4.92; λ$_{abs}$ 377 nm.

10-(Dibutylboryl)-1-(4-methylbenzoyl)-5-(pentafluorophenyl)dipyrromethane (6h-BBU$_2$). Following the procedure for 6a-BBu$_2$, reaction of 2h (0.430 g, 1.00 mmol) afforded an orange oil (0.497 g, 90%): $^1$H NMR δ 0.16-0.35 (m, 2H), 0.54-1.25 (m, 16H), 2.48 (s, 3H), 5.94-6.02 (m, 2H), 6.14-6.18 (m, 1H), 6.57 (d, J=4.0 Hz, 1H), 6.72-6.78 (m, 1H), 7.24 (d, J=4.0 Hz, 1H), 7.38 (d, J=8.0 Hz, 2H), 8.06-8.10 (br, 1H), 8.12 (d, J=8.0 Hz, 2H); $^{13}$C NMR δ 14.2, 14.4, 21.5, 21.8, 22.2, 26.1, 26.3, 27.1, 27.6, 33.7, 107.9, 109.0, 117.4, 118.3, 119.68, 119.72, 119.76, 127.7, 128.0, 130.1, 130.2, 135.0, 145.6, 146.1, 177.6; FABMS obsd 555.2627 [(M+H)$^+$], calcd 555.2606 (C$_{31}$H$_{32}$BF$_5$N$_2$O); Anal. calcd for C$_{31}$H$_{32}$BF$_5$N$_2$O: C, 67.16; H, 5.82; N, 5.05. Found: C, 67.00; H, 5.78; N, 4.91; λ$_{abs}$ 386 nm.

10-(1-Dibutylboryl)-1-(pentafluorobenzoyl)dipyrromethane (6i-BBu$_2$). Following the procedure for 6a-BBu$_2$, reaction of 2i (0.340 g, 1.00 mmol) afforded an orange oil (0.412 g, 89%): $^1$H NMR δ 0.58-0.68 (m, 2H), 0.74-0.92 (m, 10H), 1.00-1.08 (m, 2H), 1.16-1.30 (m, 4H), 4.09 (s, 2H), 6.04-6.09 (m, 1H), 6.14-6.20 (m, 1H), 6.45 (d, J=4.0 Hz, 1H), 6.70-6.75 (m, 1H), 7.01-7.06 (m, 1H), 7.90-7.93 (br, 1H); $^{13}$C NMR δ 14.4, 22.0, 26.2, 27.3, 107.6, 109.1, 117.8, 120.21, 120.26, 120.30, 121.9, 126.9, 137.5, 152.1, 164.1; FABMS obsd 465.2179 [(M+H)$^+$], calcd 465.2137 (C$_{24}$H$_{26}$BF$_5$N$_2$O); Anal. calcd for C$_{24}$H$_{26}$BF$_5$N$_2$O: C, 62.09; H, 5.64; N, 6.03. Found: C, 61.31; H, 5.63; N, 5.93; λ$_{abs}$ 382 nm.

Acylation-Boron Complexation Procedure, Exemplified for 6a-BBN. A solution of EtMgBr (20.0 mL, 20.0 mmol, 1.0 M in THF) was added slowly to a solution of 1a (2.22 g, 10.0 mmol) in THF (10 mL) under argon. The resulting mixture was stirred at room temperature for 10 min, and then cooled to –78° C. A solution of S-2-pyridyl 4-methylbenzothioate (5a, 2.29 g, 10.0 mmol) in THF (10 mL) was added. The solution was stirred at –78° C. for 10 min, then warmed to room temperature. The reaction mixture was quenched by addition of saturated aqueous NH$_4$Cl (40 mL). The mixture was extracted with ethyl acetate (30 mL). The organic layer was washed (water and brine), dried (Na$_2$SO$_4$), and filtered. The filtrate was concentrated. The crude product (a red-orange oil) thus obtained was dissolved in CH$_2$Cl$_2$ (20 mL) and treated with TEA (3.35 mL, 24.0 mmol) followed by 9-BBN-OTf (40 mL, 20.0 mmol, 0.5 M in hexane) with stirring at room temperature. A precipitate formed which largely consisted of the salt of TEA and triflic acid. After 1 h, the mixture was poured onto a pad of silica (4×8 cm) eluting with CH$_2$Cl$_2$. The product eluted as a fast-moving yellow band, which upon concentration afforded a yellow-orange solid (3.12 g, 67%) with satisfactory characterization data (mp, $^1$H NMR spectrum and FABMS) as reported above.

Note: The use of boron complexation to isolate the 1-acyldipyrromethane enables use of stoichiometric quantities of reagents rather than excess as employed previously. Thus, the 1-acylation of dipyrromethanes was conducted with slight modification to the standard procedure. Previously, 2.5 molar equiv of EtMgBr was used for the acylation of dipyrromethane (1) with 1.0 molar equiv of a Mukaiyama reagent (5) in order to avoid co-chromatography of the unreacted 5 and the product 2.[2] (The unreacted Mukaiyama reagent is consumed by EtMgBr, affording the ketone[30]). Given that the 1-acyldipyrromethane is to be isolated as a boron complex, complete consumption of the Mukaiyama reagent is not necessary.

Scale-up Procedure. A solution of EtMgBr (80.0 mL, 80.0 mmol, 1.0 M in THF) was added slowly to a solution of 1a (8.88 g, 40.0 mmol) in THF (40 mL) under argon. The resulting mixture was stirred at room temperature for 10 min, and then cooled to –78° C. A solution of S-2-pyridyl 4-methylbenzothioate (5a, 9.16 g, 40.0 mmol) in THF (40 mL) was added. The solution was stirred at –78° C. for 10 min, then warmed to room temperature. The reaction mixture was quenched by addition of saturated aqueous NH$_4$Cl. The mixture was extracted with ethyl acetate. The organic layer was dried (Na$_2$SO$_4$) and filtered. The filtrate was concentrated. The crude product (a red-orange oil) thus obtained was dissolved in toluene (80 mL) and treated with TEA (13.4 mL, 96.0 mmol) followed by 9-BBN-OTf (160 mL, 80.0 mmol, 0.5 M in hexanes) with stirring at room temperature. A precipitate formed immediately, which largely consisted of the title compound and the salt of TEA and triflic acid. After 1 h, the mixture was filtered through a Buchner funnel using coarse filter paper. The filtered material was washed with water, washed with methanol, and then dried in vacuo to afford a yellow powder (9.63 g, 52%). The filtrate was concentrated and passed through a silica pad eluting with CH$_2$Cl$_2$/hexanes afforded 1.77 g of the title compound. The combined yield is 11.4 g (62%) and the characterization data are satisfactory (mp, $^1$H NMR, $^{13}$C NMR and FABMS spectra) as reported above.

10-(9-Borabicyclo[3.3.1]non-9-yl)-1-(4-methylbenzoyl)dipyrromethane (6b-BBN). Following the acylation-complexation procedure, reaction of 1b (1.46 g, 10.0 mmol) with EtMgBr (20.0 mL, 20.0 mmol, 1.0 M in THF) followed by treatment with 5a (2.29 g, 10.0 mmol) afforded crude 2b. Boron complexation with TEA (3.35 mL, 24.0 mmol) and 9-BBN-OTf (40.0 mL, 20.0 mmol, 0.5 M in hexanes) in CH$_2$Cl$_2$ followed by passage through a pad of silica [CH$_2$Cl$_2$/hexanes (1:1)] afforded a solid which upon trituration with hexanes afforded yellow crystals (2.30 g, 60%) with satisfactory characterization data (mp, $^1$H NMR, and elemental analysis) as reported above.

10-(9-Borabicyclo[3.3.1]non-9-yl)-1-hexanoyl-5-pentyldipyrromethane (6c-BBN). Following the acylation-complexation procedure, reaction of 1e (2.16 g, 10.0 mmol) with EtMgBr (20.0 mL, 20.0 mmol, 1.0 M in THF) followed by treatment with 5f (2.09 g, 10.0 mmol) afforded crude 2c. Boron complexation with TEA (3.35 ml, 24.0 mmol) and 9-BBN-OTf (40.0 mL, 20.0 mmol, 0.5 M in hexanes) in CH$_2$Cl$_2$ followed by passage through a pad of silica [CH$_2$Cl$_2$/hexanes (1:1)] afforded an orange oil (2.59 g, 60%) with satisfactory characterization data ($^1$H NMR and $^{13}$C NMR spectra and FABMS) as reported above.

10-(9-Borabicyclo[3.3.1]non-9-yl)-1-(4-methoxybenzoyl)-5-(4-methoxyphenyl) dipyrromethane (6d-BBN). Following the acylation-complexation procedure, reaction of 1d (2.45 g, 10.0 mmol) with EtMgBr (20.0 mL, 20.0 mmol, 1.0 M in THF) followed by treatment with 5b (2.45 g, 10.0 mmol) afforded crude 2d. Boron complexation with TEA (3.35 mL, 24.0 mmol) and 9-BBN-OTf (40.0 mL, 20.0 mmol, 0.5 M in hexanes) in CH$_2$Cl$_2$ afforded a yellow-orange precipitate. The precipitate was filtered and dissolved in 50 mL of CH$_2$Cl$_2$. The solution was washed with water and brine, dried (Na$_2$SO$_4$), and concentrated to dryness. The resulting yellow solid was stirred in Et$_2$O for 1 min, filtered, washed with Et$_2$O and hexanes, dissolved in 20 mL of CH$_2$Cl$_2$ and concentrated to dryness, affording yellow crystals (2.81 g, 56%). The filtrates (from reaction mixture and stirring in Et$_2$O) were combined, concentrated, and filtered through a pad of silica CH$_2$Cl$_2$/hexanes (1:1), affording additional product (0.52 g). The total yield is 3.33 g (66%) and the characterization data are satisfactory (mp, $^1$H NMR, and elemental analysis) as reported above.

10-(Dibutylboryl)-1-(4-iodobenzoyl)-5-mesityldipyrromethane (6f-BBu$_2$). Following the acylation-complexation procedure, reaction of 1f (2.64 g, 10.0 mmol) with EtMgBr (20.0 mL, 20.0 mmol, 1.0 M in THF) followed by treatment with 5d (2.29 g, 10.0 mmol) afforded crude 2f. Boron complexation with TEA (3.35 mL, 24.0 mmol) and dibutylboron triflate (20.0 mL, 20.0 mmol, 1.0 M in CH$_2$Cl$_2$) in CH$_2$Cl$_2$ followed by passage through a pad of silica [CH$_2$Cl$_2$/hexanes (1:2)] afforded a golden-yellow amorphous powder (4.23 g, 68%) with satisfactory characterization data (mp, $^1$H NMR, and elemental analysis) as reported above.

10-(9-Borabicyclo[3.3.1]non-9-yl)-1-(4-bromobenzoyl)-5-[4-(trimethylsilylethynyl)phenyl]dipyrromethane (6g-BBN). Following the acylation-complexation procedure, reaction of 1g (3.18 g, 10.0 mmol) with EtMgBr (20.0 mL, 20.0 mmol, 1.0 M in THF) followed by treatment with 5e (2.93 g, 10.0 mmol) afforded crude 2g. Boron complexation with TEA (3.35 mL, 24.0 mmol) and 9-BBN-OTf (40.0 mL, 20.0 mmol, 0.5 M in hexanes) in CH$_2$Cl$_2$ followed by passage through a pad of silica [CH$_2$Cl$_2$/hexanes (1:1)] afforded orange-yellow crystals (4.38 g, 71%) with satisfactory characterization data (mp, $^1$H NMR, and elemental analysis) as reported above.

10-(9-Borabicyclo[3.3.1]non-9-yl)-1-(4-methylbenzoyl)-5-(pentafluorophenyl)dipyrromethane (6h-BBN). Following the acylation-complexation procedure, reaction of 1h (3.12 g, 10.0 mmol) with EtMgBr (20.0 mL, 20.0 mmol, 1.0 M in THF) followed by treatment with 5a (2.29 g, 10.0 mmol) afforded crude 2h. Boron complexation with TEA (3.35 mL, 24.0 mmol) and 9-BBN-OTf (40.0 mL, 20.0 mmol, 0.5 M in hexanes) in CH$_2$Cl$_2$ followed by passage through a pad of silica [CH$_2$Cl$_2$/hexanes (1:1)] afforded yellow crystals (3.17 g, 58%) with satisfactory characterization data (mp, $^1$H NMR, and elemental analysis) as reported above.

Decomplexation Procedure, Exemplified for 6a-BBN→2a. A solution of 6a-BBN (0.230 g, 0.500 mmol) in THF (0.8 mL) was treated with 1-pentanol (0.2 mL). The reaction mixture was heated at reflux. After 1 h, TLC (silica/CH$_2$Cl$_2$) examination showed almost complete consumption of boron complex 6a-BBN. The mixture was concentrated to dryness and the resulting oily residue was treated with 5 mL of hexanes. The oil solidified upon standing for 5 min. The mixture was heated gently under reflux for 5 min (the solid dissolved completely). The mixture was cooled, affording a precipitate upon standing for a few hours. The solvent was decanted. The solid was dissolved in a minimal amount of CH$_2$Cl$_2$ (~0.2 mL), and the title compound was precipitated upon addition of hexanes. The precipitate was collected and dried in vacuo to afford a dark-yellow powder (0.118 g, 66%). The hexanes solution was concentrated to half of the starting volume. The resulting precipitate was filtered, dissolved in a minimal volume of CH$_2$Cl$_2$ and precipitated upon addition of hexanes, affording an additional 0.030 g of title compound. The combined yield (0.148 g) is 83%: mp 64-65° C. (lit.$^2$ 70-72° C.); $^1$H NMR (CDCl$_3$) δ 2.42 (s, 3H), 5.54 (s, 1H), 5.99 (s, 1H), 6.04-6.08 (m, 1H), 6.16-6.20 (m, 1H), 6.72 (s, 1H), 6.79-6.83 (m, 1H), 7.36-7.22 (m, 8H), 7.75 (d, J=8.0 Hz, 2H), 7.97-8.00 (br, 1H) 9.34-9.37 (br, 1H); FABMS obsd 340.1593 [M$^+$], calcd 340.1576 (C$_{23}$H$_{20}$N$_2$O).

Notes: High ratios of 1-pentanol/THF can be used and result in faster reaction (20 min), but can cause interference upon crystallization. In most cases, it is important to remove 1-pentanol completely because of the high solubility of 1-acyldipyrromethanes in 1-pentanol.

1-(4-Methylbenzoyl)dipyrromethane (2b). Following the decomplexation procedure, a sample of 6b-BBN (0.74 g, 2.0 mmol) was dissolved in THF (3 mL) and 1-pentanol (1 mL) was added. The mixture was refluxed for 1 h, then concentrated and treated with 5 mL of hexanes. The resulting precipitate was filtered, washed with hexanes and dried under vacuo to give pale yellow crystals (0.43 g, 81%) with satisfactory characterization data (mp, $^1$H NMR, and elemental analysis) as described above.

1-Hexanoyl-5-pentyldipyrromethane (2c). Following the decomplexation procedure, reaction of 6c-BBN (0.869 g, 2.00 mmol) with 1-pentanol (1.00 mL, 10.0 mmol) in THF at reflux afforded a crude product. The crude product was passed through a pad of alumina [$CH_2Cl_2 \rightarrow CH_2Cl_2$/ethyl acetate (4:1)] affording a light yellow oil (0.514 g, 82%) with satisfactory characterization data ($^1$H NMR, elemental analysis) as described above.

1-(4-Methoxybenzoyl)-5-(4-methoxyphenyl)dipyrromethane (2d). Following the decomplexation procedure, a suspension of 6d-BBN (1.01 g, 2.00 mmol) in THF (3.2 mL) and 1-pentanol (0.8 mL) was refluxed for 1.5 h. The mixture was concentrated and the residue was dissolved in a small volume of $CH_2Cl_2$ and treated with hexanes. An oily precipitate was formed. The solvent was decanted. The residue was dried under vacuum, washed thoroughly with hexanes and dried again to afford a pale brown amorphous powder (0.610 g, 78%): mp 58-61° C. (dec.) (lit.[7] 113-114° C.). The $^1$H NMR data and elemental analysis data were consistent with those for the same compound obtained by a different route.[7]

1-(4-Iodobenzoyl)-5-mesityldipyrromethane (2f). A sample of 6f-BBu$_2$ (1.24 g, 2.00 mmol) was dissolved in 1-pentanol (4.0 mL). The solution was heated at 70-80° C. After 1 h the mixture was concentrated and 20 mL of hexanes was added. The mixture was heated at reflux for 2 min, and then cooled to room temperature. After standing overnight at −15° C., the precipitate was collected, dissolved in a minimum volume of $CH_2Cl_2$, and precipitated with hexanes. The precipitate was collected and dried in vacuo to afford a dark powder (0.639 g, 65%): mp 166-170° C. (lit.[2] 163° C.). The $^1$H NMR and elemental analysis data were consistent with those for the same compound obtained by a different route.[2]

5,10-Bis(4-methylphenyl)-15,20-diphenylporphyrin (8) from 6a-BBu$_2$. A sample of 1-acyldipyrromethane-boron complex 6a-BBu$_2$ (0.116 g, 0.250 mmol) was dissolved in dry THF/methanol (3:1, 6 mL) at room temperature in a round-bottomed flask fitted with a vented rubber septum and flooded with argon. The septum was removed as needed to add NaBH$_4$ (0.238 g, 6.25 mmol, 25 mol equiv) in small portions with rapid stirring. The progress of the reduction was monitored by TLC analysis [alumina, $CH_2Cl_2$/ethyl acetate (3:2)] of reaction aliquots. After the reaction was complete (about 40 min), the reaction mixture was poured into a stirred mixture of saturated aqueous NH$_4$Cl and $CH_2Cl_2$. The organic phase was separated, washed with water, dried (Na$_2$SO$_4$), and concentrated under reduced pressure to yield the monocarbinol as a foamlike solid. To the flask containing the dipyrromethane-monocarbinol (0.250 mmol assuming quantitative reduction) was added reagent-grade $CH_2Cl_2$ (50 mL). The mixture was stirred for 5 min to achieve dissolution, and then Yb(OTf)$_3$ (0.010 g, 0.016 mmol, 0.32 mM) was added. The reaction was monitored by absorption spectroscopy [by injecting a 50 μL reaction aliquot into a solution of DDQ (300 μL, 0.01 M in toluene); then 50 μL of the resulting oxidized mixture was dissolved in $CH_2Cl_2$/EtOH (3:1, 3 mL), and the absorption spectrum was recorded]. After acid-catalyzed condensation for 60 min, DDQ (0.085 mg, 0.375 mmol) was added. The mixture was stirred at room temperature for 1 h. TEA was added and the entire reaction mixture was passed through a pad of silica and eluted with $CH_2Cl_2$ until the eluant was no longer purple. The resulting porphyrin-containing solution was concentrated by rotary evaporation to give a purple solid. The solid was triturated with methanol and dried in vacuo affording a crystalline purple solid (0.021 g, 26%). The characterization data ($^1$H NMR, LDMS, and UV-vis spectra) were consistent with the reported values.[2]

5,10-Bis(4-methylphenyl)-15,20-diphenylporphyrin (8) from 6a-BBN. Following the porphyrin formation procedure for 8 from 6a-BBu$_2$, reaction of 6a-BBN (0.460 g, 1.00 mmol) afforded a purple solid (0.054 g, 17%) with satisfactory characterization data ($^1$H NMR, LDMS, and UV-vis spectra).

10-(9-Borabicyclo[3.3.1]non-9-yl)-5-phenyl-1,9-di-p-toluoyldipyrromethane (3a-BBN). A suspension of 6a-BBN (460 mg, 1.0 mmol) in THF (1 mL) and 1,1,1,3,3,3-hexamethyldisilazane (208 μL, 1.0 mmol) was treated with EtMgBr (2.20 mL, 2.20 mmol, 1 M solution in THF). The mixture was stirred at room temperature for 10 min. Then a solution of S-2-pyridyl 4-methylbenzothioate (5a, 274 mg, 1.2 mmol, 1 M solution in THF) was added. The mixture was stirred at room temperature for 0.5 h, and then the mixture was quenched by addition of a half-saturated aqueous solution of NH$_4$Cl (10 mL). Et$_2$O (10 mL) was added. The organic layer was washed with a saturated aqueous solution of NaHCO$_3$ (5 mL) followed by brine (10 mL). The organic layer was dried (Na$_2$SO$_4$) and concentrated to dryness under vacuum. The resulting brown residue (expected yield from crude NMR was 86%) was treated with small amount of Et$_2$O (~1-2 mL), affording a suspension consisting of a brown solution and a bright yellow powder. A small amount of n-hexanes was added (~2-4 mL). The resulting mixture was filtered on a Buchner funnel. The precipitate thus obtained was washed with cold methanol (2 mL) to afford a yellow powder (392 mg, 68%): $^1$H NMR δ 0.70-0.73 (m, 2H), 1.68-2.20 (m, 12H), 2.41 (s, 3H), 2.48 (s, 3H), 6.00-6.02 (m, 1H), 6.10 (s, 1H), 6.46 (d, J=4.5 Hz, 1H), 6.80-6.82 (m, 1H), 7.17-7.38 (m, 10H), 7.77 (d, J=8.4 Hz, 2H), 8.13 (d, J=8.1 Hz, 2H), 9.15 (brs, 1H); $^{13}$C NMR δ 21.8, 22.2, 23.9, 25.2, 26.2, 26.3, 30.7, 31.0, 34.5, 34.6, 45.0, 111.3, 118.5, 119.9, 120.7, 127.6, 128.1, 128.5, 129.0, 129.1, 129.2, 129.9, 130.0, 131.0, 135.2, 135.8, 140.4, 141.0, 142.5, 145.4, 150.0, 175.2, 184.3. Anal. calcd for $C_{39}H_{39}BN_2O_2$: C, 80.96; H, 6.79; N, 4.84. Found: C, 81.19; H, 6.96; N, 4.65.

Scale-up Procedure. 10-(9-Borabicyclo[3.3.1]non-9-yl)-5-phenyl-1,9-di-p-toluoyldipyrromethane (3a-BBN). A suspension of 6a-BBN (2.30 g, 5.0 mmol) in THF (5 mL) and HMDS (1.04 mL, 5.0 mmol) was treated with EtMgBr (10.0 mL, 10.0 mmol, 1 M solution in THF). The mixture was stirred at room temperature for 15 min. Then a solution of S-2-pyridyl 4-methylbenzothioate (5a, 1.26 g, 1.1 mmol, 1 M solution in THF) was added. The mixture was stirred at room temperature for 0.5 h. The mixture was quenched by addition of a half-saturated aqueous solution of NH$_4$Cl (50 mL). Et$_2$O (50 mL) was added. The organic layer was washed with aqueous NaHCO$_3$ (50 mL), water (50 mL) and brine (50 mL). The organic layer was dried (Na$_2$SO$_4$) and concentrated to dryness under vacuum. The resulting brown residue was treated with small amount of Et$_2$O (~5-10 mL), affording a suspension consisting of a brown solution and a bright yellow powder. A small amount of n-hexane was added (~10 mL). The resulting mixture was filtered on a Buchner funnel. The precipitate thus obtained was further washed with a small amount of n-hexanes (~10-20 mL) to afford a yellow powder (1.99 g, 69%): $^1$H NMR δ 0.68-0.74 (m, 2H), 1.66-2.28 (m, 12H), 2.42 (s, 3H), 2.48 (s, 3H), 6.00-6.02 (m, 1H), 6.11 (s, 1H), 6.46 (d, J=4.4 Hz, 1H), 6.81 (dd, J=4.0 Hz, J=2.4 Hz, 1H), 7.18 (d, J=8.0 Hz, 2H), 7.25-7.38 (m, 8H), 7.77 (d, J=8.4 Hz, 2H), 8.13 (d, J=8.1 Hz, 2H), 9.18 (brs, 1H); $^{13}$C NMR δ 21.8, 22.2, 23.9, 25.2, 26.2, 26.3, 30.8, 31.0, 34.6, 34.7, 45.1, 127.6, 128.2, 128.5, 129.1, 129.2, 129.3, 130.0, 130.1, 131.2, 135.3, 135.9, 140.5, 141.0, 142.5, 145.4, 150.1, 175.2, 184.3; FABMS obsd 579.3176 [(M+H)$^+$], calcd 579.3183 ($C_{39}H_{39}BN_2O_2$); Anal. calcd for $C_{39}H_{39}BN_2O_2$: C, 80.96; H, 6.79; N, 4.84. Found: C, 80.54; H, 6.70; N, 4.83.

An additional quantity of product was isolated from the filtrate as a tin complex as follows. The filtrate was concentrated to dryness. The resulting brown oily residue (~830 mg)

was dissolved in THF (2.4 mL) and treated with n-pentanol (0.6 mL). The reaction was heated at reflux. After 1 h, TLC (silica, $CH_2Cl_2$) examination showed complete consumption of the boron complex. The mixture was concentrated to dryness and the resulting dark brown oily residue was treated with TEA (0.42 mL, 3.0 mmol) and $Bu_2SnCl_2$ (0.30 g, 1.0 mmol) in $CH_2Cl_2$ (10 mL) at room temperature for 30 min. The mixture was passed through a silica pad ($CH_2Cl_2$). The eluant was concentrated to dryness. The residue was dissolved in a minimum amount of $Et_2O$. Then methanol was added, yielding a precipitate, which upon filtration afforded the dibutyl[5,10-dihydro-5-phenyl-1,9-di-p-toluoyldipyrrinato]tin(IV) complex as a pale yellow solid (190 mg, 6%).

Decomplexation of 10-(9-Borabicyclo[3.3.1]non-9-yl)-5-phenyl-1,9-di-p-toluoyldipyrromethane (3a-BBN→3a). A solution of 3a-BBN (0.289 g, 0.50 mmol) was in of THF (0.8 mL), was treated n-pentanol (0.2 mL). The reaction mixture was heated at reflux. After 1 h, TLC [silica, ethyl acetate/hexanes (4:1)] examination showed almost complete consumption of boron complex 3a-BBN. The mixture was concentrated to dryness and the resulting oily residue was treated with 5 mL of hexanes to afford a light pink solid residue. The mixture was heated gently under reflux for 5 min (the solid dissolved completely). The mixture was cooled affording a precipitate upon standing for few minutes. The solvent was decanted. The solid was dissolved in minimal amount of $CH_2Cl_2$ (~0.2 mL), and the title compound was precipitated upon addition of hexanes. The resulting mixture was filtered on a Buchner funnel. The precipitate was collected and dried in vacuo to afford a light pink powder (75 mg, 33%). The hexanes solutions was concentrated to one fourth of the starting volume, to this minimal amount of $CH_2Cl_2$ (∫0.2 mL) and filtrate of the first precipitation was added, resulting a second batch of precipitate (130 mg, 57%). The combined yield (206 mg) is 90%: $^1H$ NMR δ 2.38 (s, 3H), 5.65 (s, 1H), 5.97-5.98 (m, 2H), 6.58-6.59 (m, 2H), 7.20 (d, J=8.0 Hz, 4H), 7.31-7.33 (m, 1H), 7.34-7.42 (m, 2H), 7.48-7.50 (m, 2H), 7.70 (d, J=8.0 Hz, 4H), 11.04 (brs, 2H); FABMS obsd 458.1994 [(M+H)$^+$], calcd 458.1969 ($C_{31}H_{26}N_2O_2$).

5,15-Bis(4-methylphenyl)-10,20-diphenylporphyrin (8) from 3a-BBN. A sample of 3a-BBN (145 mg, 0.250 mmol) was dissolved in dry THF/methanol (3:1, 6 mL) at room temperature in a round-bottomed flask fitted with a vented rubber septum and flooded with argon. The septum was removed as needed to add $NaBH_4$ (946 mg, 25 mmol, 50 mol equiv) in small portions with rapid stirring. The progress of the reduction was monitored by TLC analysis [alumina, $CH_2Cl_2$/ethyl acetate (3:2)] of reaction aliquots. After the reaction was complete (about 40 min), the reaction mixture was poured into a stirred mixture of saturated aqueous $NH_4Cl$ and $CH_2Cl_2$. The organic phase was separated, washed with water, dried ($Na_2SO_4$), and concentrated under reduced pressure to yield the dicarbinol as a foamlike solid. To the flask containing the dipyrromethane-dicarbinol (0.250 mmol assuming quantitative reduction) was added reagent grade $CH_2Cl_2$ (100 mL) and 1a (55 mg, 0.250 mmol). The mixture was stirred for 5 min to achieve dissolution, and then Yb(OTf)$_3$ (206 mg, 0.325 mmol) was added. The reaction was monitored by absorption spectroscopy [Reaction monitoring was performed by injecting a 25 μL reaction aliquot into a solution of DDQ (300 μL, 0.01 M in toluene); then 25 μL of the resulting oxidized mixture was dissolved in $CH_2Cl_2$/EtOH (3:1, 3 mL), and the absorption spectrum was recorded.] Then [elapsed time of 15 min after the addition of Yb(OTf)$_3$)] DDQ (80 mg, 0.375 mmol) was added, and the mixture was stirred at room temperature for 1 h. Then TEA was added, and the entire reaction mixture was passed through a pad of alumina (to remove quinone species) and eluted with $CH_2Cl_2$ until the eluant was no longer purple. The resulting porphyrin-containing solution was concentrated to give a purple solid. The solid was triturated with methanol and dried in vacuo, affording a purple crystalline solid (32 mg, 20%). The characterization data ($^1H$ NMR, LDMS, and UV-vis spectra) were consistent with the reported values.[7]

10-(9-Borabicyclo[3.3.1]non-yl)-1-bromo-5-phenyl-9-p-toluoyldipyrromethane (9a-BBN). Following a similar procedure reported for the bromination of 1-acyldipyrromethanes,[4] a solution of 6a-BBN (464 mg, 1.00 mmol) in 10 mL of dry THF was cooled to −78° C. under Ar. NBS (178 mg, 1.00 mmol) was added and the reaction mixture was stirred for 1 h at −78° C. Hexanes (10 mL) and water (10 mL) were added and the mixture was allowed to warm to room temperature. The organic phase was extracted with hexanes, dried ($Na_2SO_4$) and concentrated under reduced pressure without heating. Column chromatography [silica, hexanes/$CH_2Cl_2$ (1:1)] afforded a yellow orange powder (505 mg, 94%): mp 53° C. (dec.); $^1H$ NMR δ 0.64-0.72 (m, 2H), 1.64-1.88 (m, 6H), 1.94-2.24 (m, 6H), 2.48 (s, 3H), 5.74-5.78 (m, 1H), 5.96 (s, 1H), 6.05-6.09 (m, 1H), 6.41 (d, J=4.0 Hz, 1H), 7.18 (d, J=8.0 Hz, 2H), 7.24-7.41 (m, 6H), 7.74 (brs, 1H), 8.12 (d, J=8.0 Hz, 2H); $^{13}C$ NMR δ 22.2, 22.9, 23.9, 25.2, 26.1, 26.4, 30.7, 30.9, 31.8, 34.57, 34.64, 44.9, 97.4, 110.2, 110.8, 118.3, 120.7, 127.4, 128.2, 128.5, 128.9, 129.9, 130.0, 133.9, 135.1, 141.6, 145.3, 151.0, 174.9; Anal. Calcd for $C_{31}H_{32}BBrN_2O$: C, 69.04; H, 5.98; N, 5.19. Found: C, 70.30; H, 6.38; N, 4.86.

REFERENCES (1) Rao, P. D.; Dhanalekshmi, S.; Littler, B. J.; Lindsey, J. S. *J. Org. Chem.* 2000, 65, 7323-7344.

(2) Rao, P. D.; Littler, B. J.; Geier, G. R., III; Lindsey, J. S. *J. Org. Chem.* 2000, 65, 1084-1092.

(3) Littler, B. J.; Ciringh, Y.; Lindsey, J. S. *J. Org. Chem.* 1999, 64, 2864-2872.

(4) Taniguchi, M.; Ra, D.; Mo, G.; Balasubramanian, T.; Lindsey, J. S. *J. Org. Chem.* 2001, 66, 7342-7354.

(5) (a) Guilard, R.; Gryko, D. T.; Canard, G.; Barbe, J.-M.; Koszama, B.; Brandes, S.; Tasior, M. *Org. Lett.* 2002, 4, 4491-4494. (b) Gryko, D. T. *Eur. J. Org. Chem.* 2002, 1735-1743. (c) Decréau, R. A.; Collman, J. P. *Tetrahedron Lett.* 2003, 44, 3323-3327. (d) Gryko, D. T.; Tasior, M.; Koszama, B. *J. Porphyrins Phthalocyanines* 2003, 7, 239-248.

(6) Lee, C.-H.; Li, F.; Iwamoto, K.; Dadok, J.; Bothner-By, A. A.; Lindsey, J. S. *Tetrahedron* 1995, 51, 11645-11672.

(7) Tamaru, S.-I.; Yu, L.; Youngblood, W. J.; Muthukumaran, K.; Taniguchi, M.; Lindsey, J. S. *J. Org. Chem.* 2004, 69, 765-777.

(8) Mehta, P.; Mehta, R. K. *J. Indian Chem. Soc.* 1984, LXI, 571-572.

(9) Hübler, K.; Hübler, U. *Z. Anorg. Allg. Chem.* 2000, 626, 1224-1236.

(10) Dawson, D. M.; Walker, D. A.; Thornton-Pett, M.; Bochmann, M. *J. Chem. Soc. Dalton Trans.* 2000, 459-466.

(11) Adams, H.; Bailey, N. A.; Fenton, D. E.; Moss, S.; Rodriguez de Barbarin, C. O. *J. Chem. Soc. Dalton Trans.* 1986, 693-699.

(12) Bacchi, A.; Bonardi, A.; Carcelli, M.; Mazza, P.; Pelagatti, P.; Pelizzi, C.; Pelizzi, G.; Solinas, C.; Zani, F. *J. Inorg. Biochem.* 1998, 69, 101-112.

(13) Treibs, A.; Kreuzer, F.-H. *Liebigs Ann. Chem.* 1968, 718, 208-223.

(14) (a) Wagner, R. W.; Lindsey, J. S. *Pure Appl. Chem.* 1996, 68, 1373-1380. Corrigendum: Wagner, R. W.; Lindsey, J. S. *Pure Appl. Chem.* 1998, 70 (8), p. i. (b) Burghart, A.; Kim, H.; Welch, M. B.; Thoresen, L. H.; Reibenspies, J.; Burgess, K. *J. Org. Chem.* 1999, 64, 7813-7819. (c) Kim, H.; Burghart, A.; Welch, M. B.; Reibenspies, J.; Burgess, K. *Chem. Commun.* 1999, 1889-1890. (d) Burghart, A.; Thoresen, L. H.; Chen, J.; Burgess, K.; Bergström, F.; Johansson, L. B.-Å. *Chem. Commun.* 2000, 2203-2204. (e) Chen, J.; Burghart, A.; Derecskei-Kovacs, A.; Burgess, K. *J. Org. Chem.* 2000, 65, 2900-2906. (f) Ambroise, A.; Kirmaier, C.; Wagner, R. W.; Loewe, R. S.; Bocian, D. F.; Holten, D.; Lindsey, J. S. *J. Org. Chem.* 2002, 67, 3811-3826. (g) Gabe, Y.; Urano, Y.; Kikuchi, K.; Kojima, H.; Nagano, T. *J. Am. Chem. Soc.* 2004, 126, 3357-3367.

(15) Chen, J.; Burghart, A.; Wan, C.-W.; That, L.; Ortiz, C.; Reibenspies, J.; Burgess, K. *Tetraheclron Lett.* 2000, 41, 2303-2307.

(16) Minkin, V. I.; Korobov, M. S.; Nivorozhkin, L. E.; Kompan, O. E.; Borodkin, G. S.; Olekhnovich, R. Ya. *Russ. J. Coord. Chem.* 1998, 24, 152-161.

(17) Köster, R.; Bellut, H.; Hattori, S.; Weber, L. *Liebigs Ann. Chem.* 1968, 720, 32-57.

(18) Bellut, H.; Köster, R. *Liebigs Ann. Chem.* 1970, 738, 86-96.

(19) Bellut, H.; Miller, C. D.; Köster, R. *Synth. Inorg. Metal-Org. Chem. I* 1971, 83-91.

(20) Kerschl, S.; Wraclmeyer, B. *J. Chem. Soc., Chem. Commun.* 1986, 403-404.

(21) Wrackmeyer, B.; Maisel, H. E.; Schwarze, B.; Milius, W.; Köster, R. *J. Organonmet. Chem.* 1997, 541, 97-107.

(22) Wrackmeyer, B.; Schwarze, B. *J. Organomet. Chem.* 1997, 534, 181-186.

(23) Wrackmeyer, B.; Schwarze, B. *J. Organomet. Chem.* 1997, 534, 207-211.

(24) Wrackmeyer, B.; Schwarze, B.; Milius, W. *J. Organomet. Chem.* 1997, 545-546, 297-308.

(25) Wrackmeyer, B.; Schwarze, B.; Milius, W.; Boese, R.; Parchment, O. G.; Webb, G. A. *J. Organomet. Chem.* 1997, 552, 247-254.

(26) (a) Cornelissen-Gude, C.; Retting, W. *J. Phys. Chem. A* 1999, 103, 4371-4377. (b) Kehr, G.; Fröhlich, R.; Wibbeling, B.; Erker, G. *Chem. Eur. J.* 2000, 6, 258-266.

(27) Tomizaki, K.-Y.; Lysenko, A. B.; Taniguchi, M.; Lindsey, J. S. *Tetrahedron* 2004, 60, 2011-2023.

(28) Wrackmeyer, B. *Ann Rep. NMR Spectroscopy* 1988, 20, 61-203.

(29) English, R. B.; McGillivray, G.; Smal, E. *Acta Cryst.* 1980, B36, 1136-1141.

(30) Araki, M.; Sakata, S.; Takei, H.; Mukaiyama, T. *Bull. Chem. Soc. Jpn.* 1974, 47, 1777-1780.

(31) Laha, J. K.; Dhanalekshmi, S.; Taniguchi, M.; Ambroise, A.; Lindsey, J. S. *Org. Process Res. Dev.* 2003, 7, 799-812.

(32) Cho, W.-S.; Kim, H.-J.; Littler, B. J.; Miller, M. A.; Lee, C.-H.; Lindsey, J. S. *J. Org. Chem.* 1999, 64, 7890-7901.

(33) Geier, G. R., III; Callinan, J. B.; Rao, P. D.; Lindsey, J. S. *J. Porphyrins Phthalocyanines* 2001, 5, 810-823.

(34) Bar-Haim, G.; Kol, M. *J. Org. Chem.* 1997, 62, 6682-6683.

(35) Bar-Haim, G.; Kol, M. *Tetrahedron Lett.* 1998, 39, 2643-2644.

(36) (a) Fenyo, D.; Chait, B. T.; Johnson, T. E.; Lindsey, J. S. *J. Porphyrins Phthalocyanines* 1997, 1, 93-99. (b) Srinivasan, N.; Haney, C. A.; Lindsey, J. S.; Zhang, W.; Chait, B. T. *J. Porphyrins Phthalocyanines* 1999, 3, 283-291.

(37) Araki, M.; Sakata, S.; Takei, H.; Mukaiyama, T. *Bull. Chem. Soc. Jpn.* 1974, 47, 1777-1780.

(38) Fraser, R. R.; Mansour, T. S. *J. Org. Chem.* 1984, 49, 3442-3443.

(39) Yang, K.-C.; Chang, C.-C.; Huang, J.-Y.; Lin, C.-C.; Lee, G.-H.; Wang, Y.; Chiang, M. Y. *J. Organomet. Chem.* 2002, 648, 176-187.

(40) Nicolaou, K. C.; Claremon, D. A.; Papahatjis, D. P. *Tetrahedron Lett.* 1981, 22, 4647-4650.

The foregoing is illustrative of the present invention, and is not to be construed as limiting thereof. The invention is defined by the following claims, with equivalents of the claims to be included therein.

That which is claimed is:

1. A method of making a metal complex, comprising:
   (a) providing a 1-monoacyldipyrromethane; and then
   (b) combining said 1-monoacyldipyrromethane with a compound of the formula $R^1R^2MX$, wherein:
   M is boron,
   $R^1$ and $R^2$ are each independently selected from the group consisting of alkyl, alkenyl, alkynyl, and aryl, each of which can be unsubstituted or substituted one or more times with a substituent selected from the group consisting of alkyl, alkenyl, alkynyl, aryl, alkoxy, alkylcarbonyl, alkylcarbonyloxy, alkylsulfinyl, alkylsulfonyl, alkylthio, halo, cyano, nitro, sulfo, oxo, formyl, azido, and carbamoyl; and
   X is an anion leaving group;
   to produce a metal complex of the formula $DMR^1R^2$, wherein DH is said 1-monoacyldipyrromethane.

2. The method of claim 1, wherein said combining step is carried out by combining a mixture containing said 1-monoacyldipyrromethane with said compound of the formula $R^1R^2MX$.

3. The method of claim 1 wherein said combining step is carried out in a solution and said metal complex is solubilized or suspended in said solution, said method further comprising the steps of:
   (c) combining said metal complex with a hindered alkyl amine base in an organic solvent to form a solid comprising said metal complex; and then
   (d) separating said solid from said organic solvent.

4. The method of claim 3, wherein said hindered alkyl amine base is selected from the group consisting of triethylamine, diisopropylethylamine, and triphenylamine.

5. The method of claim 3, wherein said solvent comprises dichloromethane.

6. The method of claim 1, further comprising the step of
   (c) decomplexing said 1-monoacyldipyrromethane from said metal complex by combining said metal complex with an hydroxide, an alcohol, water, or combination thereof.

7. The method of claim 1, wherein said compound of formula $R^1R^2MX$ is immobilized on a solid support, said method further comprising the step of:
   (c) releasing said 1-monoacyldipyrromethane complex from said solid support.

* * * * *

UNITED STATES PATENT AND TRADEMARK OFFICE
CERTIFICATE OF CORRECTION

PATENT NO. : 7,423,160 B2 Page 1 of 1
APPLICATION NO. : 11/846630
DATED : September 9, 2008
INVENTOR(S) : Lindsey et al.

It is certified that error appears in the above-identified patent and that said Letters Patent is hereby corrected as shown below:

In the Claims:

Column 13, Lines 49 - 50:
Please correct
 "known (H, Chart 3).$^{16}$ W
  ught that"

To read:
 -- known (H, Chart 3).$^{16}$
  We thought that --

Signed and Sealed this

Twenty-fifth Day of November, 2008

JON W. DUDAS
*Director of the United States Patent and Trademark Office*